(12) United States Patent
Smith et al.

(10) Patent No.: US 9,783,503 B2
(45) Date of Patent: *Oct. 10, 2017

(54) CRYSTALLINE FORMS OF AN ESTROGEN RECEPTOR MODULATOR

(71) Applicant: Genentech, Inc., South San Francisco, CA (US)

(72) Inventors: Nicholas D. Smith, San Diego, CA (US); Mark R. Herbert, Ramona, CA (US)

(73) Assignee: GENENTECH, INC., South San Francisco, CA (US)

( * ) Notice: Subject to any disclaimer, the term of this patent is extended or adjusted under 35 U.S.C. 154(b) by 81 days.

This patent is subject to a terminal disclaimer.

(21) Appl. No.: 14/821,931

(22) Filed: Aug. 10, 2015

(65) Prior Publication Data

US 2016/0039770 A1 Feb. 11, 2016

Related U.S. Application Data

(60) Provisional application No. 62/036,015, filed on Aug. 11, 2014.

(51) Int. Cl.
 *C07D 231/56* (2006.01)
(52) U.S. Cl.
 CPC .................. *C07D 231/56* (2013.01)
(58) Field of Classification Search
 CPC .................................................. C07D 231/56
 See application file for complete search history.

(56) References Cited

U.S. PATENT DOCUMENTS

| 8,299,112 | B2 * | 10/2012 | Smith | C07D 209/08 |
| | | | | 514/406 |
| 8,455,534 | B2 * | 6/2013 | Smith | C07D 209/08 |
| | | | | 514/406 |
| 9,399,646 | B2 * | 7/2016 | Smith | C07D 209/08 |
| 2007/0134803 | A1 * | 6/2007 | Blatter | B01J 19/0046 |
| | | | | 436/96 |
| 2012/0071535 | A1 * | 3/2012 | Smith | C07D 209/08 |
| | | | | 514/406 |
| 2013/0231333 | A1 | 9/2013 | Smith et al. | |
| 2015/0105403 | A1 | 4/2015 | Smith et al. | |
| 2015/0157606 | A1 | 6/2015 | Maneval | |
| 2015/0258080 | A1 | 9/2015 | Hager | |
| 2015/0258099 | A1 | 9/2015 | Hager | |

FOREIGN PATENT DOCUMENTS

| WO | 2012/037410 A2 | 3/2012 |
| WO | 2012/037411 A2 | 3/2012 |
| WO | 2013/142266 A1 | 9/2013 |
| WO | 2014/151899 A1 | 9/2014 |

OTHER PUBLICATIONS

Background Information for the October ACPS Meeting, FDA, 2002.*
B. Rodriquez-Spong et al. Advanced Drug Delivery Reviews, 2004, 56, pp. 241-274.*
Luo et al. Cell, 2009, 136, pp. 823-837.*
Govek et al., "Optimization of an indazole series of selective estrogen receptor degraders: Tumor regression in a tamoxifen-resistant breast cancer xenograft" Bioorg Med Chem Lett. 25(22):5163-7 ( 2015).
ISR for WO2016/023847, PCT/EP2015/068327, 2015.
Lai et al., "Identification of GDC-0810 (ARN-810), an Orally Bioavailable Selective Estrogen Receptor Degrader (SERD) that Demonstrates Robust Activity in Tamoxifen-Resistant Breast Cancer Xenografts" Journal of Medicinal Chemistry 58(12):4888-4904 ( 2015).

* cited by examiner

*Primary Examiner* — Matthew Coughlin
(74) *Attorney, Agent, or Firm* — Kevin M. Clark

(57) ABSTRACT

Described herein are amorphous and crystalline forms of pharmaceutically acceptable salts of the estrogen receptor modulator (E)-3-(4-((E)-2-(2-chloro-4-fluorophenyl)-1-(1H-indazol-5-yl)but-1-en-1-yl) phenyl)acrylic acid. Also described are pharmaceutical compositions suitable for administration to a mammal that include the estrogen receptor modulator, and methods of using the estrogen receptor modulator, alone and in combination with other compounds, for treating diseases or conditions that are associated with estrogen receptor activity.

28 Claims, 6 Drawing Sheets

CRYSTALLINE FORMS OF AN ESTROGEN RECEPTOR MODULATOR

CROSS REFERENCE TO RELATED APPLICATIONS

This non-provisional application filed under 37 CFR §1.53(b), claims the benefit under 35 USC §119(e) of U.S. Provisional Application Ser. No. 62/036,015 filed on 11 Aug. 2014, which is incorporated by reference in entirety.

FIELD OF THE INVENTION

Described herein is the estrogen receptor modulator (E)-3-(4-((E)-2-(2-chloro-4-fluorophenyl)-1-(1H-indazol-5-yl)but-1-en-1-yl)phenyl)acrylic acid, pharmaceutically acceptable salts, solvates, and crystalline forms thereof.

BACKGROUND OF THE INVENTION

The estrogen receptor ("ER") is a ligand-activated transcriptional regulatory protein that mediates induction of a variety of biological effects through its interaction with endogenous estrogens. Endogenous estrogens include 17β-estradiol and estrones. ER has been found to have two isoforms, ER-α and ER-β.

Estrogens and estrogen receptors are implicated in a number of diseases or conditions, such as breast cancer, lung cancer, ovarian cancer, colon cancer, prostate cancer, endometrial cancer, uterine cancer, as well as others diseases or conditions.

SUMMARY OF THE INVENTION

Described herein is (E)-3-(4-((E)-2-(2-chloro-4-fluorophenyl)-1-(1H-indazol-5-yl)but-1-en-1-yl)phenyl)acrylic acid, pharmaceutically acceptable salts, pharmaceutically acceptable solvates (including hydrates), polymorphs, and amorphous phases thereof, and methods of uses thereof.

In one aspect, described herein is a pharmaceutically acceptable salt of (E)-3-(4-((E)-2-(2-chloro-4-fluorophenyl)-1-(1H-indazol-5-yl)but-1-en-1-yl)phenyl)acrylic acid, wherein the pharmaceutically acceptable salt is in crystalline form. In some embodiments, the pharmaceutically acceptable salt is a potassium salt, magnesium, a L-arginine salt, choline salt, ethylenediamine salt, N-methyl glucamine salt, tromethamine salt, or hydroxyethylpyrrolidine salt, wherein the pharmaceutically acceptable salt is in crystalline form. In some embodiments, the pharmaceutically acceptable salt is a N-methyl glucamine salt, wherein the pharmaceutically acceptable salt is in crystalline form.

In one aspect, described herein is a crystalline Form 1 of (E)-3-(4-((E)-2-(2-chloro-4-fluorophenyl)-1-(1H-indazol-5-yl)but-1-en-1-yl)phenyl)acrylic acid, N-methyl glucamine salt that is characterized as having:
  (a) an X-Ray powder diffraction (XRPD) pattern substantially the same as shown in FIG. 1;
  (b) an X-ray powder diffraction (XRPD) pattern with characteristic peaks at 4.7±0.1° 2-Theta, 9.4±0.1° 2-Theta, 12.3±0.1° 2-Theta, 14.1±0.1° 2-Theta, 17.3±0.1° 2-Theta, 18.7±0.1° 2-Theta, 19.9±0.1° 2-Theta, 20.2±0.1° 2-Theta, 21.5±0.1° 2-Theta, 24.3±0.1° 2-Theta, 24.7±0.1° 2-Theta;
  (c) substantially the same X-ray powder diffraction (XRPD) pattern post storage at 40° C. and 75% RH for at least a week;
  (d) substantially the same X-ray powder diffraction (XRPD) pattern post storage at 25° C. and 96% RH for at least a week;
  (e) a DSC thermogram with an endotherm having an onset temperature at about 149° C.;
  (f) a DSC thermogram substantially similar to the one set forth in FIG. 2;
  (g) A TGA thermogram with 2 weight loses observed between 30-86° C., water loss and 199-346° C. degradation;
  (h) A TGA thermogram substantially similar to the one set forth in FIG. 3;
  (i) an observed aqueous solubility that is greater than 10 mg/mL;
  or
  (j) combinations thereof.

In another aspect, described herein is a crystalline Pattern 2 of (E)-3-(4-((E)-2-(2-chloro-4-fluorophenyl)-1-(1H-indazol-5-yl)but-1-en-1-yl)phenyl)acrylic acid, N-methyl glucamine salt that is characterized as having:
  (a) an X-Ray powder diffraction (XRPD) pattern substantially the same as shown in FIG. 4;
  (b) an X-ray powder diffraction (XRPD) pattern with characteristic peaks at 4.1±0.1° 2-Theta, 8.3±0.1° 2-Theta, 12.4±0.1° 2-Theta, 16.6±0.1° 2-Theta, 19.4±0.1° 2-Theta, 20.1±0.1° 2-Theta, 20.6±0.1° 2-Theta, 21.9±0.1° 2-Theta, 23.0±0.1° 2-Theta, 25.0±0.1° 2-Theta;
  (c) an X-ray powder diffraction (XRPD) pattern post storage at 40° C. and 75% RH for at least a week that is substantially the same as that observed for the crystalline Form 1 of (E)-3-(4-((E)-2-(2-chloro-4-fluorophenyl)-1-(1H-indazol-5-yl)but-1-en-1-yl)phenyl)acrylic acid, N-methyl glucamine salt;
  (d) a DSC thermogram with an endotherm having an onset temperature at about 121° C.;
  (e) a DSC thermogram substantially similar to the one set forth in FIG. 5;
  (f) a TGA thermogram with 3 weight loses observed between 40-102° C., 102-143° C., and 143-346° C. degradation;
  (g) A TGA thermogram substantially similar to the one set forth in FIG. 6; or
  (h) combinations thereof.

Also described herein is a pharmaceutical composition comprising a crystalline form of a pharmaceutically salt of (E)-3-(4-((E)-2-(2-chloro-4-fluorophenyl)-1-(1H-indazol-5-yl)but-1-en-1-yl)phenyl)acrylic acid, and at least one additional ingredient selected from pharmaceutically acceptable carriers, diluents and excipients. In some embodiments, the pharmaceutically salt of (E)-3-(4-((E)-2-(2-chloro-4-fluorophenyl)-1-(1H-indazol-5-yl)but-1-en-1-yl)phenyl)acrylic acid is a N-methyl glucamine salt. In some embodiments, the pharmaceutical composition is in a form suitable for oral administration to a mammal. In some embodiments, the pharmaceutical composition is in an oral solid dosage form. In some embodiments, the pharmaceutical composition comprises about 0.5 mg to about 1000 mg of crystalline (E)-3-(4-((E)-2-(2-chloro-4-fluorophenyl)-1-(1H-indazol-5-yl)but-1-en-1-yl)phenyl)acrylic acid, N-methyl glucamine salt.

In some embodiments, described herein is a pharmaceutical composition comprising a crystalline form of (E)-3-(4-((E)-2-(2-chloro-4-fluorophenyl)-1-(1H-indazol-5-yl)but-1-en-1-yl)phenyl)acrylic acid, N-methyl glucamine salt as described herein, and at least one additional ingredient selected from pharmaceutically acceptable carriers, diluents and excipients. In some embodiments, the pharmaceutical composition includes Form 1 of (E)-3-(4-((E)-2-(2-chloro-4-fluorophenyl)-1-(1H-indazol-5-yl)but-1-en-1-yl)phenyl) acrylic acid, N-methyl glucamine salt. In some embodiments, the pharmaceutical composition includes Pattern 2 of (E)-3-(4-((E)-2-(2-chloro-4-fluorophenyl)-1-(1H-indazol-5-yl)but-1-en-1-yl)phenyl)acrylic acid, N-methyl glucamine salt. In some embodiments, the pharmaceutical composition is in a form suitable for oral administration to a mammal. In some embodiments, the pharmaceutical composition is in an oral dosage form. In some embodiments, the pharmaceutical composition is in an oral solid dosage form. In some embodiments, the pharmaceutical composition is in the form of a tablet, pill, or capsule. In some embodiments, the pharmaceutical composition is in the form of a capsule. In some embodiments, the pharmaceutical composition is in the form of an immediate release capsule or an enteric coated capsule. In some embodiments, the pharmaceutical composition is in the form of a tablet. In some embodiments, the pharmaceutical composition is in the form of an immediate release tablet, an enteric coated tablet, or a sustained release tablet. In some embodiments, the pharmaceutical composition is in the form of a moisture barrier coated tablet. In some embodiments, the pharmaceutical composition comprises about 0.5 mg to about 1000 mg of crystalline (E)-3-(4-((E)-2-(2-chloro-4-fluorophenyl)-1-(1H-indazol-5-yl)but-1-en-1-yl)phenyl)acrylic acid, N-methyl glucamine salt. In some embodiments, the pharmaceutical composition comprises about 10 mg to about 400 mg of crystalline (E)-3-(4-((E)-2-(2-chloro-4-fluorophenyl)-1-(1H-indazol-5-yl)but-1-en-1-yl)phenyl)acrylic acid, N-methyl glucamine salt.

Also provided is an article of manufacture comprising multiple unit doses of the oral solid dosage form pharmaceutical composition described herein in a high-density polyethylene (HDPE) bottle equipped with a high-density polyethylene (HDPE) cap. In some embodiments, high-density polyethylene (HDPE) bottle further comprises an aluminum foil induction seal and silica gel desiccant.

Also described herein is (E)-3-(4-((E)-2-(2-chloro-4-fluorophenyl)-1-(1H-indazol-5-yl)but-1-en-1-yl)phenyl)acrylic acid, N-methyl glucamine salt that is in amorphous form. Also described herein is a pharmaceutical composition comprising amorphous (E)-3-(4-((E)-2-(2-chloro-4-fluorophenyl)-1-(1H-indazol-5-yl)but-1-en-1-yl)phenyl)acrylic acid, N-methyl glucamine salt, and at least one additional ingredient selected from pharmaceutically acceptable carriers, diluents and excipients. In some embodiments, the pharmaceutical composition is in a form suitable for oral administration to a mammal. In some embodiments, the pharmaceutical composition is in an oral solid dosage form.

In one aspect, described herein is the use of a crystalline form of a pharmaceutically salt of (E)-3-(4-((E)-2-(2-chloro-4-fluorophenyl)-1-(1H-indazol-5-yl)but-1-en-1-yl)phenyl) acrylic acid in the treatment of cancer in a mammal. In another aspect, described herein is the use of crystalline (E)-3-(4-((E)-2-(2-chloro-4-fluorophenyl)-1-(1H-indazol-5-yl)but-1-en-1-yl)phenyl)acrylic acid, N-methyl glucamine salt in the treatment of cancer in a mammal. In another aspect, described herein is the use of amorphous (E)-3-(4-((E)-2-(2-chloro-4-fluorophenyl)-1-(1H-indazol-5-yl)but-1-en-1-yl)phenyl)acrylic acid, N-methyl glucamine salt in the treatment of cancer in a mammal. In some embodiments, the cancer is amenable to treatment with an estrogen receptor modulator. In some embodiments, the cancer is breast cancer, ovarian cancer, endometrial cancer, prostate cancer, lung cancer or uterine cancer.

In certain embodiments described herein, a crystalline form of a pharmaceutically salt of (E)-3-(4-((E)-2-(2-chloro-4-fluorophenyl)-1-(1H-indazol-5-yl)but-1-en-1-yl)phenyl) acrylic acid is used in the manufacture of medicaments for the treatment or prevention of diseases, disorders, or conditions associated with estrogen receptor activity.

Also described is a method of treating cancer in a mammal comprising administering to the mammal a crystalline pharmaceutically acceptable salt of (E)-3-(4-((E)-2-(2-chloro-4-fluorophenyl)-1-(1H-indazol-5-yl)but-1-en-1-yl) phenyl)acrylic acid. In some embodiments, the crystalline pharmaceutically acceptable salt of (E)-3-(4-((E)-2-(2-chloro-4-fluorophenyl)-1-(1H-indazol-5-yl)but-1-en-1-yl) phenyl)acrylic acid is (E)-3-(4-((E)-2-(2-chloro-4-fluorophenyl)-1-(1H-indazol-5-yl)but-1-en-1-yl)phenyl)acrylic acid, N-methyl glucamine salt. In some embodiments, the cancer is breast cancer, ovarian cancer, endometrial cancer, prostate cancer, lung cancer, or uterine cancer. In some embodiments, the cancer is breast cancer. In some embodiments, the method further comprises administering at least one additional therapeutic agent to the mammal. In some embodiments, the at least one additional therapeutic agent is an anti-cancer agent.

Also described is a method of treating cancer in a mammal comprising administering to the mammal a pharmaceutical composition as described herein. In some embodiments, the cancer is breast cancer, ovarian cancer, endometrial cancer, prostate cancer, lung cancer, or uterine cancer. In some embodiments, the cancer is breast cancer.

Also provided is the use of (E)-3-(4-((E)-2-(2-chloro-4-fluorophenyl)-1-(1H-indazol-5-yl)but-1-en-1-yl)phenyl) acrylic acid, N-methyl glucamine salt for the manufacture of a medicament for the treatment or prevention of cancer in a human. Further provided is the use of (E)-3-(4-((E)-2-(2-chloro-4-fluorophenyl)-1-(1H-indazol-5-yl)but-1-en-1-yl) phenyl)acrylic acid, N-methyl glucamine salt for the manufacture of a medicament for the treatment or prevention of cancer in a human wherein the cancer is breast cancer, ovarian cancer, endometrial cancer, prostate cancer, lung cancer, or uterine cancer. In some embodiments, (E)-3-(4-((E)-2-(2-chloro-4-fluorophenyl)-1-(1H-indazol-5-yl)but-1-en-1-yl)phenyl)acrylic acid, N-methyl glucamine salt is crystalline.

Also described herein are processes for the preparation of crystalline form of a pharmaceutically acceptable salt of (E)-3-(4-((E)-2-(2-chloro-4-fluorophenyl)-1-(1H-indazol-5-yl)but-1-en-1-yl)phenyl)acrylic acid.

Also described herein are processes for the preparation of crystalline (E)-3-(4-((E)-2-(2-chloro-4-fluorophenyl)-1-(1H-indazol-5-yl)but-1-en-1-yl)phenyl)acrylic acid, N-methyl glucamine salt. The disclosed processes provide for the preparation of crystalline ((E)-3-(4-((E)-2-(2-chloro-4-fluorophenyl)-1-(1H-indazol-5-yl)but-1-en-1-yl)phenyl) acrylic acid, N-methyl glucamine salt in good yield and high purity.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this detailed description.

DETAILED DESCRIPTION OF THE INVENTION

Figure 1:
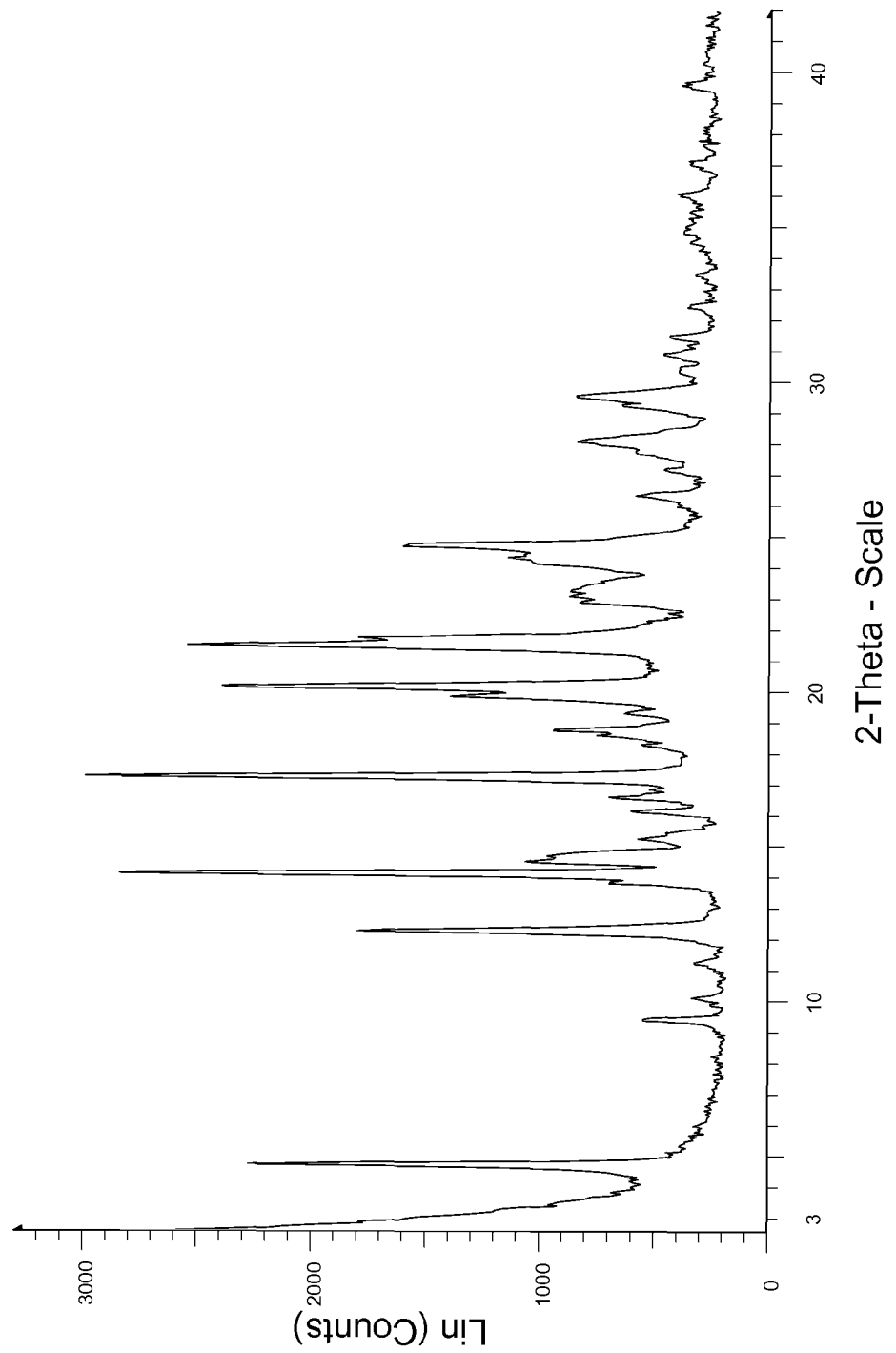
FIG. 1 illustrates the XRPD of Form 1 of crystalline (E)-3-(4-((E)-2-(2-chloro-4-fluorophenyl)-1-(1H-indazol-5-yl)but-1-en-1-yl)phenyl)acrylic acid, N-methyl glucamine salt.

Breast cancer is the most common form of cancer and the leading cause of cancer death in women worldwide. Approximately 80% of all breast cancers express and are dependent on the estrogen receptor (ER) for tumor growth and progression. Modulation of estrogen activity and/or synthesis is the mainstay of therapeutic approach in postmenopausal women with ER-positive (ER+) breast cancer. However, despite the effectiveness of available hormonal therapies such as tamoxifen, aromatase inhibitors (e.g., anastrozole, letrozole and exemestane) and full ER antagonists/degraders (e.g., fulvestrant), many patients ultimately relapse or develop resistance to these agents and therefore require further treatment for optimal disease control. As such, there is a need for the development of new ER-targeting therapies with increased anti-tumor activity to further delay disease progression and/or overcome resistance to the currently available hormonal therapies and ultimately prolong survival in postmenopausal women with ER+ advanced breast cancer.

Despite becoming refractory to aromatase inhibitors or tamoxifen, growth and survival of resistant tumor cells remain dependent on ER signaling; therefore, patients with ER+ breast cancer can still respond to second/third line hormonal treatment after progression on prior hormonal therapy. In some embodiments, in the endocrine resistant state, ER can signal in a ligand-independent manner. In some embodiments, an agent with a dual mechanism of action such as ER antagonism plus degradation has the potential to target both ligand-dependent and independent ER signaling and, consequently, improve treatment outcomes in late stage ER+ breast cancer.

Breast Cancer Stages

The stages of breast cancer are based on a number of factors, such as the size of the tumor, if cancer is found in the lymph nodes, and how far the cancer has spread. The stages are numbered 0, I, II, III or IV, with Stage I being the least advanced stage and Stage IV being the most advanced. Stage 0 is considered non-invasive breast cancer. Stages I-II is considered early breast cancer. Stage III is considered locally advanced breast cancer. Stage IV is considered metastatic breast cancer. These descriptions are broad descriptions of breast cancer stages, and may not include all possibilities.

In some embodiments, Stages I, IIA, and IIB (and some cancers of stage IIIA) are considered early breast cancer. At these stages, the cancer has not spread beyond the breast or the axillary lymph nodes (those under the arm).

In some embodiments, locally advanced breast cancer includes Stages IIIA, IIIB and IIIC. In some embodiments, Stage IIIA breast cancer includes instances when the tumor size is not large but the cancer has spread to many axillary (under the arm) lymph nodes or lymph nodes near the breastbone. In some other embodiments, Stage IIIA breast cancer includes instances when the tumor is large but there is less lymph node spread. Stage IIIB describes breast cancer in which the tumor has spread to the chest wall or the skin of the breast and may or may not have spread to lymph nodes. Stage IIIC describes cancer that has spread to lymph nodes below or above the collarbone, to many axillary (under the arm) lymph nodes, or to lymph nodes near the breastbone. The tumor may be of any size.

Stage IV describes metastatic breast cancer, which is cancer that has spread from the breast to other parts of the body, such as the bones (bone metastases) or the liver, lungs, or brain (visceral metastases).

(E)-3-(4-((E)-2-(2-Chloro-4-fluorophenyl)-1-(1H-indazol-5-yl)but-1-en-1-yl)phenyl)acrylic acid is a small molecule non-steroidal ERα antagonist that competes with estrogens for binding to the estrogen receptor with low nanomolar potency. In contrast to first generation ER antagonists, such as tamoxifen, (E)-3-(4-((E)-2-(2-chloro-4-fluorophenyl)-1-(1H-indazol-5-yl)but-1-en-1-yl)phenyl) acrylic acid fully antagonizes the response of ER to estrogens and induces proteosomal degradation of ER-α in breast cancer cell lines. These bipartite activities result in full antagonism of ER-target gene transcription in breast cancer cell lines in vitro. The result is robust inhibition of ER signaling, and in turn, inhibition of breast tumor cell proliferation. Unlike fulvestrant, which is also an ER antagonist and degrader, (E)-3-(4-((E)-2-(2-chloro-4-fluorophenyl)-1-(1H-indazol-5-yl)but-1-en-1-yl)phenyl)acrylic acid has a nonsteroidal chemical backbone and displays good oral bioavailability.

In vivo, (E)-3-(4-((E)-2-(2-chloro-4-fluorophenyl)-1-(1H-indazol-5-yl)but-1-en-1-yl)phenyl)acrylic acid exhibited dose dependent anti-tumor activity in both tamoxifen-sensitive and tamoxifen-resistant xenograft models of ER+ breast cancer. Efficacious doses include 1-100 mg/kg/day. Efficacy in tamoxifen-resistant xenograft models correlated with efficient antagonist activity on ER target genes and reduction of ER-α tumor levels. Despite displaying similar transcriptional and ER degrader activities, fulvestrant appeared to be less efficacious than (E)-3-(4-((E)-2-(2-chloro-4-fluorophenyl)-1-(1H-indazol-5-yl)but-1-en-1-yl) phenyl)acrylic acid in some of these models.

Disclosed herein is the use of (E)-3-(4-((E)-2-(2-chloro-4-fluorophenyl)-1-(1H-indazol-5-yl)but-1-en-1-yl)phenyl) acrylic acid, or a pharmaceutically acceptable salt thereof, in the treatment of locally advanced or metastatic estrogen receptor positive breast cancer in a postmenopausal woman. In some embodiments, the breast cancer is locally advanced or metastatic estrogen receptor positive, human epidermal growth factor receptor 2 negative (HER2−) breast cancer. In some embodiments, the breast cancer in the postmenopausal woman had previously progressed in the presence of hormonal therapy. In some embodiments, the breast cancer is not amenable to resection or radiation therapy with curative intent. In some embodiments, the breast cancer has progressed after at least 6 months of hormonal therapy for estrogen receptor positive breast cancer. In some embodiments, the breast cancer in the postmenopausal woman had previously progressed in the presence of therapy with fulvestrant. In some embodiments, a pharmaceutically acceptable salt of (E)-3-(4-((E)-2-(2-chloro-4-fluorophenyl)-1-(1H-indazol-5-yl)but-1-en-1-yl)phenyl)acrylic acid is used. In some embodiments, the pharmaceutically acceptable salt of (E)-3-(4-((E)-2-(2-chloro-4-fluorophenyl)-1-(1H-indazol-5-yl)but-1-en-1-yl)phenyl)acrylic acid is crystalline.

In another aspect, described herein is the use of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, in the treatment of hormone receptor positive metastatic breast cancer in a postmenopausal woman with disease progression following antiestrogen therapy. In some embodiments, the hormone receptor positive metastatic breast cancer is estrogen receptor positive metastatic breast cancer. In some embodiments, the estrogen receptor positive metastatic breast cancer is human epidermal growth factor receptor 2 negative (HER2−) breast cancer. In some embodiments, a pharmaceutically acceptable salt of (E)-3-(4-((E)-2-(2-chloro-4-fluorophenyl)-1-(1H-indazol-5-yl)but-1-en-1-yl)phenyl)acrylic acid is used. In some embodiments, the pharmaceutically acceptable salt of (E)-3-(4-((E)-2-(2-chloro-4-fluorophenyl)-1-(1H-indazol-5-yl)but-1-en-1-yl)phenyl)acrylic acid is crystalline.

Given the central role of ER-α in breast cancer development and progression, (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is useful in the treatment of breast cancer, either alone or in combination with other agent agents that can modulate other critical pathways in breast cancer, including but not limited to those that target IGF1R, EGFR, CDK 4/6, erB-B2 and 3 the PI3K/AKT/mTOR axis, HSP90, PARP or histone deacetylases.

Given the central role of ER-α in breast cancer development and progression, (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is useful in the treatment of breast cancer, either alone or in combination with other agent used to treat breast cancer.

In some embodiments, (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is used in the treatment of an estrogen receptor dependent or estrogen receptor mediated disease or condition in mammal. ER-related diseases or conditions include ER-α dysfunction is associated with cancer (bone cancer, breast cancer, lung cancer, colorectal cancer, endometrial cancer, prostate cancer, ovarian and uterine cancer), central nervous system (CNS) defects (alcoholism, migraine), cardiovascular system defects (aortic aneurysm, susceptibility to myocardial infarction, aortic valve sclerosis, cardiovascular disease, coronary artery disease, hypertension), hematological system defects (deep vein thrombosis), immune and inflammation diseases (Graves' Disease, arthritis, multiple sclerosis, cirrhosis), susceptibility to infection (hepatitis B, chronic liver disease), metabolic defects (bone density, cholestasis, hypospadias, obesity, osteoarthritis, osteopenia, osteoporosis), neurological defects (Alzheimer's disease, Parkinson's disease, migraine, vertigo), psychiatric defects (anorexia nervosa, attention deficit hyperactivity disorder (ADHD), dementia, major depressive disorder, psychosis) and reproductive defects (age of menarche, endometriosis, infertility. In some embodiments, the estrogen receptor dependent or estrogen receptor mediated disease or condition is selected from cancer, central nervous system (CNS) defects, cardiovascular system defects, hematological system defects, immune and inflammation diseases, susceptibility to infection, metabolic defects, neurological defects, psychiatric defects and reproductive defects. In some embodiments, the estrogen receptor dependent or estrogen receptor mediated disease or condition is selected from bone cancer, breast cancer, lung cancer, colorectal cancer, endometrial cancer, prostate cancer, ovarian cancer, uterine cancer, alcoholism, migraine, aortic aneurysm, susceptibility to myocardial infarction, aortic valve sclerosis, cardiovascular disease, coronary artery disease, hypertension, deep vein thrombosis, Graves' Disease, arthritis, multiple sclerosis, cirrhosis, hepatitis B, chronic liver disease, bone density, cholestasis, hypospadias, obesity, osteoarthritis, osteopenia, osteoporosis, Alzheimer's disease, Parkinson's disease, migraine, vertigo, anorexia nervosa, attention deficit hyperactivity disorder (ADHD), dementia, major depressive disorder, psychosis, age of menarche, endometriosis, and infertility. In some embodiments, a pharmaceutically acceptable salt of (E)-3-(4-((E)-2-(2-chloro-4-fluorophenyl)-1-(1H-indazol-5-yl)but-1-en-1-yl)phenyl)acrylic acid is used. In some embodiments, the pharmaceutically acceptable salt of (E)-3-(4-((E)-2-(2-chloro-4-fluorophenyl)-1-(1H-indazol-5-yl)but-1-en-1-yl)phenyl)acrylic acid is crystalline.

In some embodiments, (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is used to treat cancer in a mammal. In some embodiments, the cancer is breast cancer, ovarian cancer, endometrial cancer, prostate cancer, or uterine cancer. In some embodiments, the cancer is breast cancer, lung cancer, ovarian cancer, endometrial cancer, prostate cancer, or uterine cancer. In some embodiments, the cancer is breast cancer. In some embodiments, the cancer is ovarian cancer. In some embodiments, the cancer is endometrial cancer. In some embodiments, the cancer is prostate cancer. In some embodiments, the cancer is uterine cancer. In some embodiments, the cancer is lung cancer. In some embodiments, the cancer is a hormone dependent cancer. In some embodiments, the cancer is an estrogen receptor dependent cancer. In some embodiments, the cancer is an estrogen-sensitive cancer. In some embodiments, the cancer is resistant to anti-hormonal treatment. In some embodiments, the cancer is an estrogen-sensitive cancer or an estrogen receptor dependent cancer that is resistant to anti-hormonal treatment. In some embodiments, the cancer is a hormone-sensitive cancer or a hormone receptor dependent cancer that is resistant to anti-hormonal treatment. In some embodiments, anti-hormonal treatment includes treatment with at least one agent selected from tamoxifen, fulvestrant, steroidal aromatase inhibitors, and non-steroidal aromatase inhibitors. In some embodiments, a pharmaceutically acceptable salt of (E)-3-(4-((E)-2-(2-chloro-4-fluorophenyl)-1-(1H-indazol-5-yl)but-1-en-1-yl)phenyl)acrylic acid is used. In some embodiments, the pharmaceutically acceptable salt of (E)-3-(4-((E)-2-(2-chloro-4-fluorophenyl)-1-(1H-indazol-5-yl)but-1-en-1-yl)phenyl)acrylic acid is crystalline.

In some embodiments, (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is used to treat hormone receptor positive metastatic breast cancer in a postmenopausal woman with disease progression following anti-estrogen therapy. In some embodiments, a pharmaceutically acceptable salt of (E)-3-(4-((E)-2-(2-chloro-4-fluorophenyl)-1-(1H-indazol-5-yl)but-1-en-1-yl)phenyl)acrylic acid is used. In some embodiments, the pharmaceutically acceptable salt of (E)-3-(4-((E)-2-(2-chloro-4-fluorophenyl)-1-(1H-indazol-5-yl)but-1-en-1-yl)phenyl)acrylic acid is crystalline.

In some embodiments, (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is used to treat a hormonal dependent benign or malignant disease of the breast or reproductive tract in a mammal. In some embodiments, the benign or malignant disease is breast cancer. In some embodiments, a pharmaceutically acceptable salt of (E)-3-(4-((E)-2-(2-chloro-4-fluorophenyl)-1-(1H-indazol-5-yl)but-1-en-1-yl)phenyl)acrylic acid is used. In some embodiments, the pharmaceutically acceptable salt of (E)-3-(4-((E)-2-(2-chloro-4-fluorophenyl)-1-(1H-indazol-5-yl)but-1-en-1-yl)phenyl)acrylic acid is crystalline.

In some embodiments, methods of treatment with (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, includes a treatment regimen that includes administering radiation therapy to the mammal. In some embodiments, a pharmaceutically acceptable salt of (E)-3-(4-((E)-2-(2-chloro-4-fluorophenyl)-1-(1H-indazol-5-yl)but-1-en-1-yl)phenyl)acrylic acid is used. In some embodiments, the pharmaceutically acceptable salt of (E)-3-(4-((E)-2-(2-chloro-4-fluorophenyl)-1-(1H-indazol-5-yl)but-1-en-1-yl)phenyl)acrylic acid is crystalline.

In some embodiments, methods of treatment with (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, includes administering the compound prior to or following surgery. In some embodiments, a pharmaceutically acceptable salt of (E)-3-(4-((E)-2-(2-chloro-4-fluorophenyl)-1-(1H-indazol-5-yl)but-1-en-1-yl)phenyl)acrylic acid is used. In some embodiments, the pharmaceutically acceptable salt of (E)-3-(4-((E)-2-(2-chloro-4-fluorophenyl)-1-(1H-indazol-5-yl)but-1-en-1-yl)phenyl)acrylic acid is crystalline.

In some embodiments, methods of treatment with (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, includes administering to the mammal at least one additional anti-cancer agent. In some embodiments, a pharmaceutically acceptable salt of (E)-3-(4-((E)-2-(2-chloro-4-fluorophenyl)-1-(1H-indazol-5-yl)but-1-en-1-yl)phenyl)acrylic acid is used. In some embodiments, the pharmaceutically acceptable salt of (E)-3-(4-((E)-2-(2-chloro-4-fluorophenyl)-1-(1H-indazol-5-yl)but-1-en-1-yl)phenyl)acrylic acid is crystalline.

In some embodiments, (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is used to treat cancer in a mammal, wherein the mammal is chemotherapy-naïve. In some embodiments, a pharmaceutically acceptable salt of (E)-3-(4-((E)-2-(2-chloro-4-fluorophenyl)-1-(1H-indazol-5-yl)but-1-en-1-yl)phenyl)acrylic acid is used. In some embodiments, the pharmaceutically acceptable salt of (E)-3-(4-((E)-2-(2-chloro-4-fluorophenyl)-1-(1H-indazol-5-yl)but-1-en-1-yl)phenyl)acrylic acid is crystalline.

In some embodiments, (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is used in the treatment of cancer in a mammal. In some embodiments, (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is used to treat cancer in a mammal, wherein the mammal is being treated for cancer with at least one anti-cancer agent. In one embodiment, the cancer is a hormone refractory cancer. In some embodiments, a pharmaceutically acceptable salt of (E)-3-(4-((E)-2-(2-chloro-4-fluorophenyl)-1-(1H-indazol-5-yl)but-1-en-1-yl)phenyl) acrylic acid is used. In some embodiments, the pharmaceutically acceptable salt of (E)-3-(4-((E)-2-(2-chloro-4-fluorophenyl)-1-(1H-indazol-5-yl)but-1-en-1-yl)phenyl)acrylic acid is crystalline.

In some embodiments, (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is used in the treatment or prevention of diseases or conditions of the uterus in a mammal. In some embodiments, the disease or condition of the uterus is leiomyoma, uterine leiomyoma, endometrial hyperplasia, or endometriosis. In some embodiments, the disease or condition of the uterus is a cancerous disease or condition of the uterus. In some other embodiments, the disease or condition of the uterus is a non-cancerous disease or condition of the uterus. In some embodiments, a pharmaceutically acceptable salt of (E)-3-(4-((E)-2-(2-chloro-4-fluorophenyl)-1-(1H-indazol-5-yl)but-1-en-1-yl)phenyl)acrylic acid is used. In some embodiments, the pharmaceutically acceptable salt of (E)-3-(4-((E)-2-(2-chloro-4-fluorophenyl)-1-(1H-indazol-5-yl)but-1-en-1-yl)phenyl)acrylic acid is crystalline.

In some embodiments, (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is used in the treatment of endometriosis in a mammal. In some embodiments, a pharmaceutically acceptable salt of (E)-3-(4-((E)-2-(2-chloro-4-fluorophenyl)-1-(1H-indazol-5-yl)but-1-en-1-yl)phenyl)acrylic acid is used. In some embodiments, the pharmaceutically acceptable salt of (E)-3-(4-((E)-2-(2-chloro-4-fluorophenyl)-1-(1H-indazol-5-yl)but-1-en-1-yl)phenyl)acrylic acid is crystalline.

In some embodiments, (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is used in the treatment of leiomyoma in a mammal. In some embodiments, the leiomyoma is a uterine leiomyoma, esophageal leiomyoma, cutaneous leiomyoma, or small bowel leiomyoma. In some embodiments, (E)-3-(4-((E)-2-(2-chloro-4-fluorophenyl)-1-(1H-indazol-5-yl)but-1-en-1-yl)phenyl) acrylic acid, or a pharmaceutically acceptable salt thereof, is used in the treatment of fibroids in a mammal. In some embodiments, (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, is used in the treatment of uterine fibroids in a mammal. In some embodiments, a pharmaceutically acceptable salt of (E)-3-(4-((E)-2-(2-chloro-4-fluorophenyl)-1-(1H-indazol-5-yl)but-1-en-1-yl)phenyl)acrylic acid is used. In some embodiments, the pharmaceutically acceptable salt of (E)-3-(4-((E)-2-(2-chloro-4-fluorophenyl)-1-(1H-indazol-5-yl)but-1-en-1-yl)phenyl)acrylic acid is crystalline.

(E)-3-(4-((E)-2-(2-Chloro-4-fluorophenyl)-1-(1H-indazol-5-yl)but-1-en-1-yl)phenyl)acrylic acid "(E)-3-(4-((E)-2-(2-Chloro-4-fluorophenyl)-1-(1H-indazol-5-yl)but-1-en-1-yl)phenyl)acrylic acid" refers to the compound with the following structure:

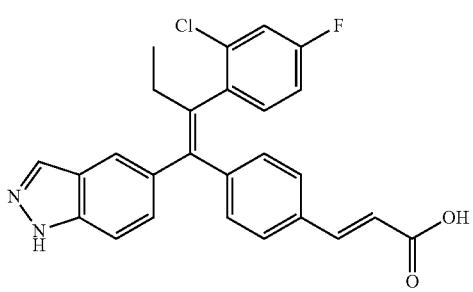 [SMILES: CC/C(=C(/c1ccc(/C=C/C(=O)O)cc1)c1ccc2[nH]ncc2c1)c1ccc(F)cc1Cl]

(E)-3-(4-((E)-2-(2-Chloro-4-fluorophenyl)-1-(1H-indazol-5-yl)but-1-en-1-yl)phenyl)acrylic acid is described in US Patent Publication no. 2013/0231333.

Pharmaceutically acceptable salts of (E)-3-(4-((E)-2-(2-chloro-4-fluorophenyl)-1-(1H-indazol-5-yl)but-1-en-1-yl)phenyl)acrylic acid include, but are not limited to: (1) acid addition salts, formed by reacting the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when the acidic proton present in the compound is replaced by a metal ion, e.g., an alkali metal ion (e.g. lithium, sodium, potassium), an alkaline earth ion (e.g. magnesium, or calcium), or an aluminum ion. In some cases, the compound coordinates with an organic base, such as, but not limited to, ethanolamine, diethanolamine, triethanolamine, tromethamine, N-methylglucamine (NMG), dicyclohexylamine, tris(hydroxymethyl)methylamine. In other cases, the compound herein forms a salt with an amino acid such as, but not limited to, arginine, lysine, and the like. Acceptable inorganic bases used to form a salt with the compound, include, but are not limited to, aluminum hydroxide, calcium hydroxide, potassium hydroxide, sodium carbonate, sodium hydroxide, and the like.

In some embodiments, described herein is a pharmaceutically acceptable salt of (E)-3-(4-((E)-2-(2-chloro-4-fluorophenyl)-1-(1H-indazol-5-yl)but-1-en-1-yl)phenyl)acrylic acid. In some embodiments, described herein is a pharmaceutically acceptable salt of (E)-3-(4-((E)-2-(2-chloro-4-fluorophenyl)-1-(1H-indazol-5-yl)but-1-en-1-yl)phenyl)acrylic acid, wherein the pharmaceutically acceptable salt is a sodium salt, an ammonium salt, a lysine salt, calcium salt, potassium salt, magnesium, a L-arginine salt, choline salt, ethylenediamine salt, N-methyl glucamine salt, tromethamine salt, or hydroxyethylpyrrolidine salt. In some embodiments, described herein is a crystalline form of a pharmaceutically acceptable salt of (E)-3-(4-((E)-2-(2-chloro-4-fluorophenyl)-1-(1H-indazol-5-yl)but-1-en-1-yl)phenyl) acrylic acid, wherein the pharmaceutically acceptable salt is a potassium salt, magnesium, a L-arginine salt, choline salt, ethylenediamine salt, N-methyl glucamine salt, tromethamine salt, or hydroxyethylpyrrolidine salt. In some embodiments, the pharmaceutically acceptable salt of (E)-3-(4-((E)-2-(2-chloro-4-fluorophenyl)-1-(1H-indazol-5-yl)but-1-en-1-yl)phenyl)acrylic acid is a potassium salt, choline salt, or N-methyl glucamine salt. In some embodiments, the pharmaceutically acceptable salt of (E)-3-(4-((E)-2-(2-chloro-4-fluorophenyl)-1-(1H-indazol-5-yl)but-1-en-1-yl)phenyl) acrylic acid is a N-methyl glucamine salt.

(E)-3-(4-((E)-2-(2-Chloro-4-fluorophenyl)-1-(1H-indazol-5-yl)but-1-en-1-yl)phenyl)acrylic acid, N-methyl glucamine salt "(E)-3-(4-((E)-2-(2-Chloro-4-fluorophenyl)-1-(1H-indazol-5-yl)but-1-en-1-yl)phenyl)acrylic acid, N-methyl glucamine salt", "(E)-3-(4-((E)-2-(2-chloro-4-fluorophenyl)-1-(1H-indazol-5-yl)but-1-en-1-yl)phenyl)acrylic acid, NMG salt" or "(2S,3R,4R,5R)-2,3,4,5,6-pentahydroxy-N-methylhexan-1-aminium (E)-3-(4-((E)-2-(2-chloro-4-fluorophenyl)-1-(1H-indazol-5-yl)but-1-enyl)phenyl)acrylate" refers to the compound with the following structure:

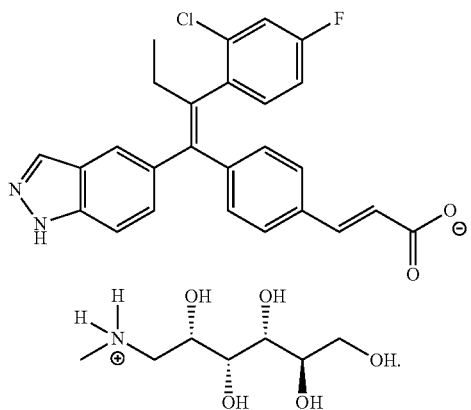

Amorphous (E)-3-(4-((E)-2-(2-Chloro-4-fluorophenyl)-1-(1H-indazol-5-yl)but-1-en-1-yl)phenyl)acrylic acid, N-methyl glucamine salt In some embodiments, (E)-3-(4-((E)-2-(2-chloro-4-fluorophenyl)-1-(1H-indazol-5-yl)but-1-en-1-yl)phenyl)acrylic acid, N-methyl glucamine salt is amorphous. In some embodiments, the amorphous phase of (E)-3-(4-((E)-2-(2-chloro-4-fluorophenyl)-1-(1H-indazol-5-yl)but-1-en-1-yl)phenyl)acrylic acid, N-methyl glucamine salt has an XRPD pattern showing a lack of crystallinity.

Form 1

Figure 2:
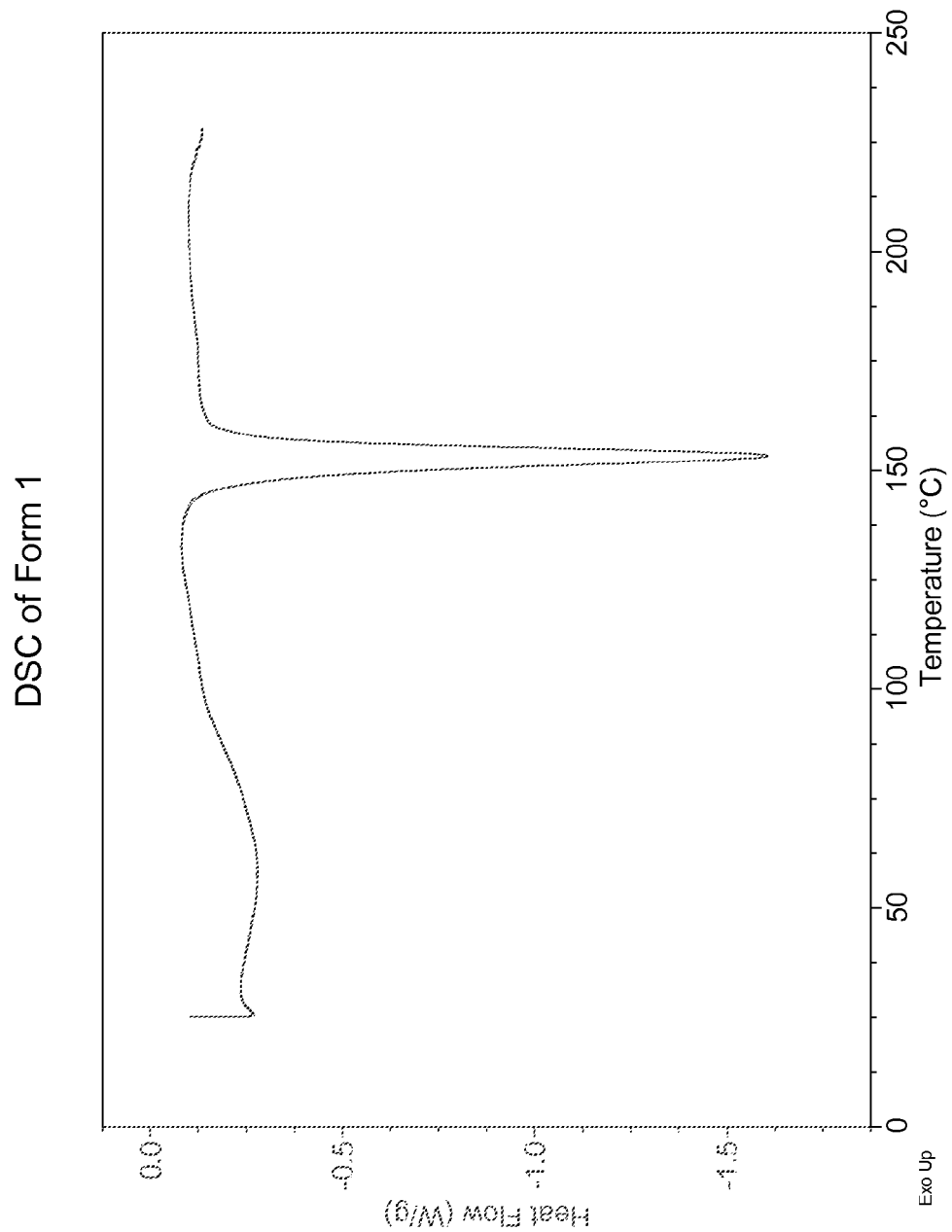
FIG. 2 illustrates the DSC thermogram of Form 1 of crystalline (E)-3-(4-((E)-2-(2-chloro-4-fluorophenyl)-1-(1H-indazol-5-yl)but-1-en-1-yl)phenyl)acrylic acid, N-methyl glucamine salt.
Figure 3:
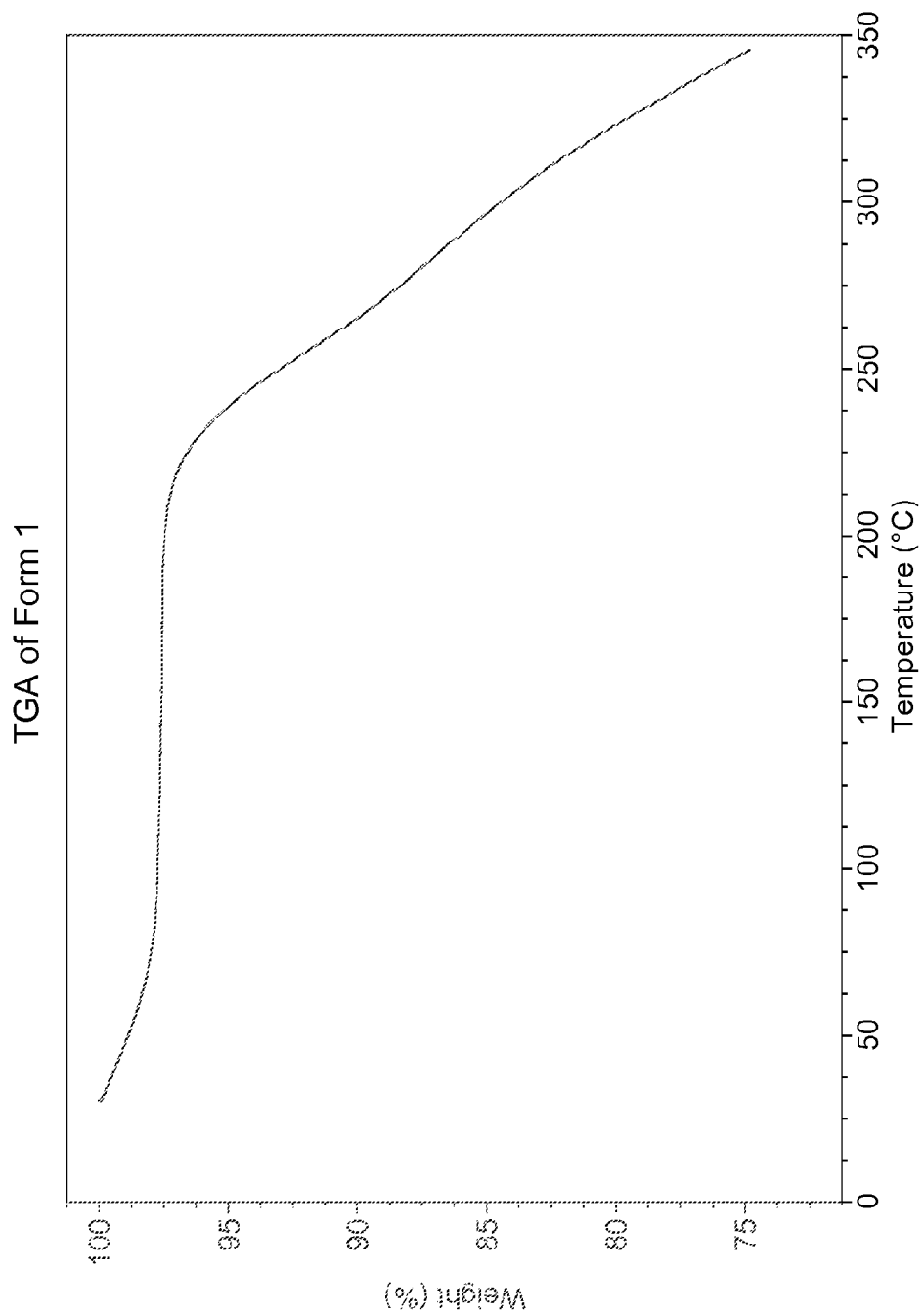
FIG. 3 illustrates the TGA thermogram of Form 1 of crystalline (E)-3-(4-((E)-2-(2-chloro-4-fluorophenyl)-1-(1H-indazol-5-yl)but-1-en-1-yl)phenyl)acrylic acid, N-methyl glucamine salt.

In some embodiments, (E)-3-(4-((E)-2-(2-chloro-4-fluorophenyl)-1-(1H-indazol-5-yl)but-1-en-1-yl)phenyl)acrylic acid, N-methyl glucamine salt is crystalline. In some embodiments, described herein is a crystalline Form 1 of (E)-3-(4-((E)-2-(2-chloro-4-fluorophenyl)-1-(1H-indazol-5-yl)but-1-en-1-yl)phenyl)acrylic acid, N-methyl glucamine salt. In some embodiments, Form 1 of (E)-3-(4-((E)-2-(2-chloro-4-fluorophenyl)-1-(1H-indazol-5-yl)but-1-en-1-yl)

phenyl)acrylic acid, N-methyl glucamine salt is characterized as having:

an X-Ray powder diffraction (XRPD) pattern substantially the same as shown in FIG. 1;

an X-ray powder diffraction (XRPD) pattern with characteristic peaks at 4.7±0.1° 2-Theta, 9.4±0.1° 2-Theta, 12.3±0.1° 2-Theta, 14.1±0.1° 2-Theta, 17.3±0.1° 2-Theta, 18.7±0.1° 2-Theta, 19.9±0.1° 2-Theta, 20.2±0.1° 2-Theta, 21.5±0.1° 2-Theta, 24.3±0.1° 2-Theta, 24.7±0.1° 2-Theta;

substantially the same X-ray powder diffraction (XRPD) pattern post storage at 40° C. and 75% RH for at least a week;

substantially the same X-ray powder diffraction (XRPD) pattern post storage at 25° C. and 96% RH for at least a week;

a DSC thermogram with an endotherm having an onset temperature at about 149° C.;

a DSC thermogram substantially similar to the one set forth in FIG. 2;

A TGA thermogram with 2 weight loses observed between 30-86° C., water loss and 199-346° C. degradation;

A TGA thermogram substantially similar to the one set forth in FIG. 3;

an observed aqueous solubility that is greater than 10 mg/mL;

or combinations thereof.

In some embodiments, Form 1 has an X-Ray powder diffraction (XRPD) pattern substantially the same as shown in FIG. 1.

In some embodiments, Form 1 has an X-ray powder diffraction (XRPD) pattern with characteristic peaks at 4.7±0.1° 2-Theta, 9.4±0.1° 2-Theta, 12.3±0.1° 2-Theta, 14.1±0.1° 2-Theta, 17.3±0.1° 2-Theta, 18.7±0.1° 2-Theta, 19.9±0.1° 2-Theta, 20.2±0.1° 2-Theta, 21.5±0.1° 2-Theta, 24.3±0.1° 2-Theta, 24.7±0.1° 2-Theta.

In some embodiments, Form 1 has substantially the same X-ray powder diffraction (XRPD) pattern post storage at 40° C. and 75% RH for at least a week.

In some embodiments, Form 1 has substantially the same X-ray powder diffraction (XRPD) pattern post storage at 25° C. and 96% RH for at least a week.

In some embodiments, Form 1 has a DSC thermogram with an endotherm having an onset temperature at about 149° C.

In some embodiments, Form 1 has a DSC thermogram substantially similar to the one set forth in FIG. 2.

In some embodiments, Form 1 has a TGA thermogram with 2 weight loses observed between 30-86° C., water loss and 199-346° C. degradation.

In some embodiments, Form 1 has a TGA thermogram substantially similar to the one set forth in FIG. 3.

In some embodiments, Form 1 has an observed aqueous solubility that is greater than 10 mg/mL.

In some embodiments, Form 1 is characterized as having properties (a), (b), (c), (d), (e), (f) (g), (h), and (i).

In some embodiments, Form 1 was obtained from 1,4 dioxane, toluene, tert-butylmethyl ether (TBME), tetralin, anisole, butyl acetate, ethyl acetate, isopropyl acetate, isopropyl alcohol (IPA), 1,2-dimethoxyethane (DME), dichloromethane (DCM), methyl isobutyl ketone (MIBK), methyl ethyl ketone (MEK), acetone, methanol, ethanol, acetonitrile, or nitromethane, or a combination thereof.

Pattern 2

Figure 4:
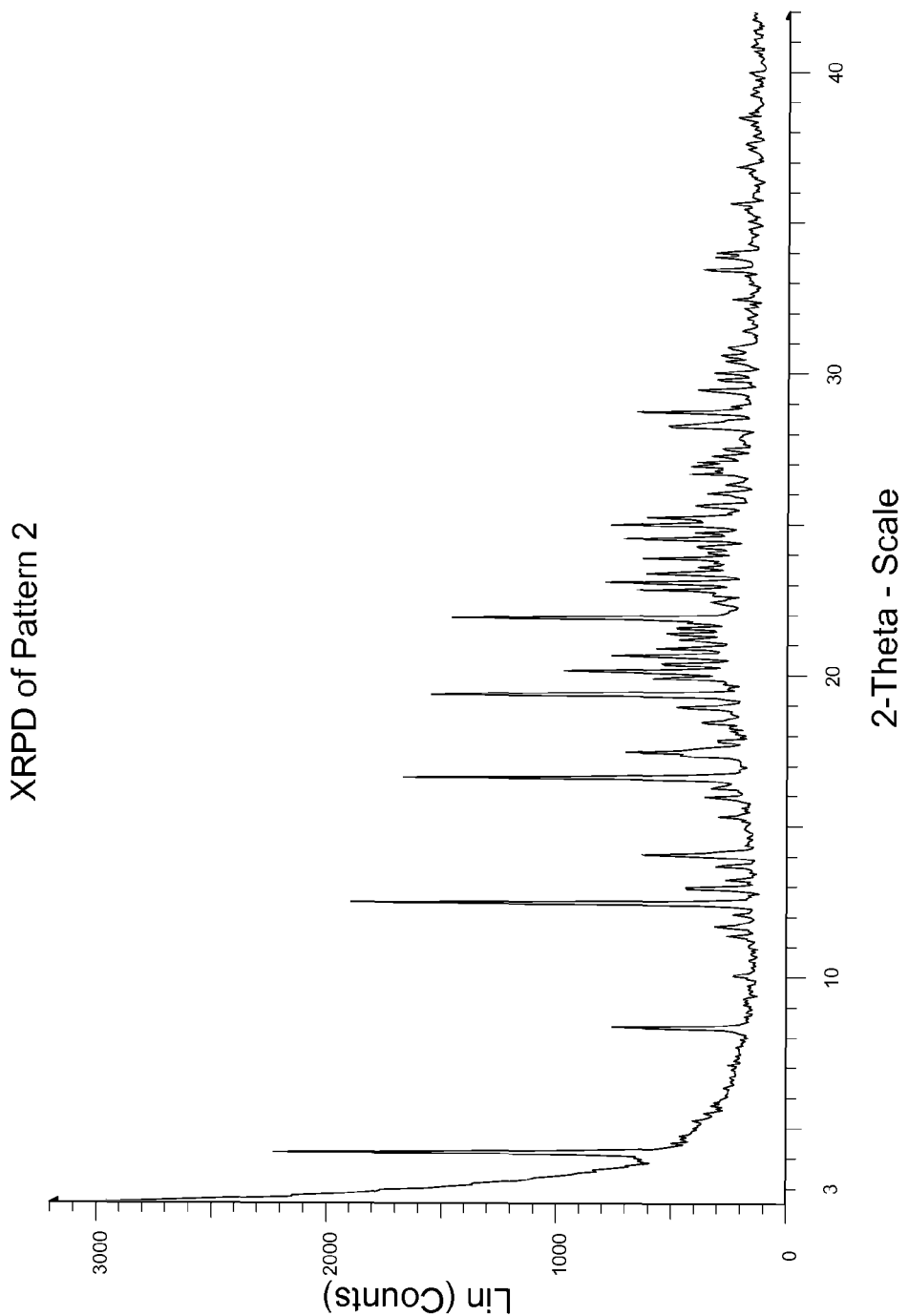
FIG. 4 illustrates the XRPD of Pattern 2 of crystalline (E)-3-(4-((E)-2-(2-chloro-4-fluorophenyl)-1-(1H-indazol-5-yl)but-1-en-1-yl)phenyl)acrylic acid, N-methyl glucamine salt.
Figure 5:
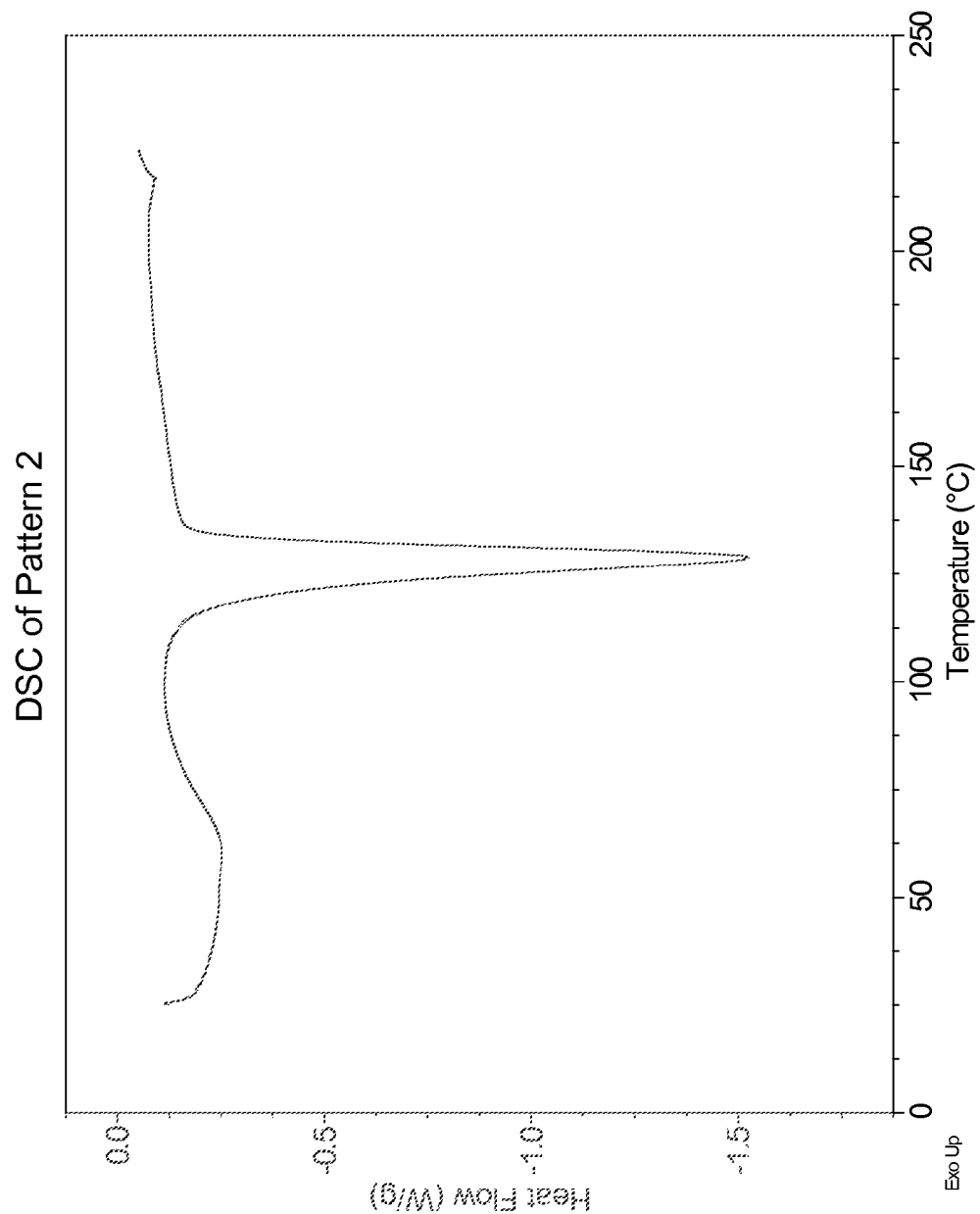
FIG. 5 illustrates the DSC thermogram of Pattern 2 of crystalline (E)-3-(4-((E)-2-(2-chloro-4-fluorophenyl)-1-(1H-indazol-5-yl)but-1-en-1-yl)phenyl)acrylic acid, N-methyl glucamine salt.
Figure 6:
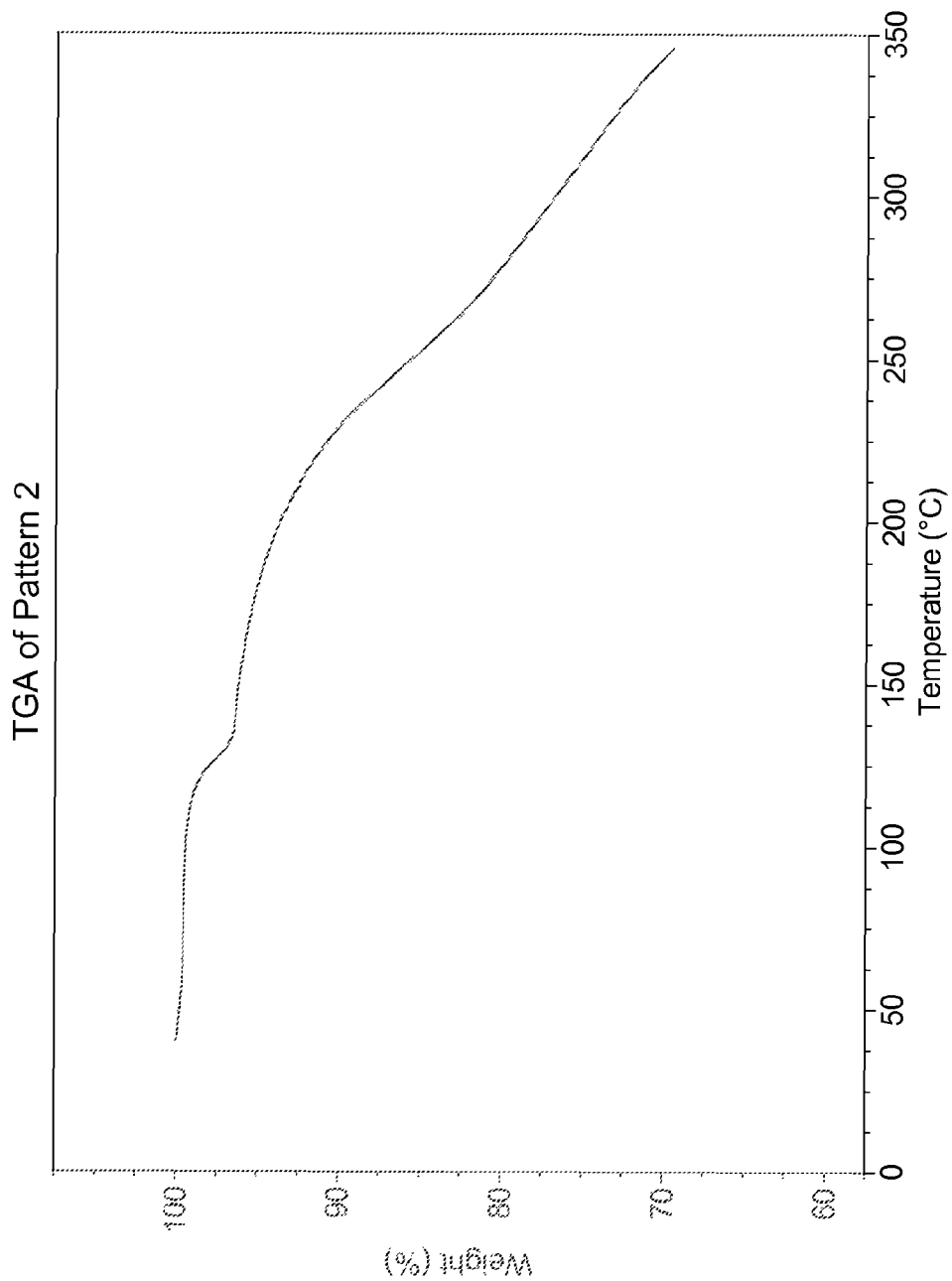
FIG. 6 illustrates the TGA thermogram of Pattern 2 of crystalline (E)-3-(4-((E)-2-(2-chloro-4-fluorophenyl)-1-(1H-indazol-5-yl)but-1-en-1-yl)phenyl)acrylic acid, N-methyl glucamine salt.

In some embodiments, (E)-3-(4-((E)-2-(2-chloro-4-fluorophenyl)-1-(1H-indazol-5-yl)but-1-en-1-yl)phenyl)acrylic acid, N-methyl glucamine salt is crystalline. In some embodiments, described herein is a crystalline Pattern 2 of (E)-3-(4-((E)-2-(2-chloro-4-fluorophenyl)-1-(1H-indazol-5-yl)but-1-en-1-yl)phenyl)acrylic acid, N-methyl glucamine salt. In some embodiments, Pattern 2 of (E)-3-(4-((E)-2-(2-chloro-4-fluorophenyl)-1-(1H-indazol-5-yl)but-1-en-1-yl)phenyl)acrylic acid, N-methyl glucamine salt is characterized as having:

an X-Ray powder diffraction (XRPD) pattern substantially the same as shown in FIG. 4;

an X-ray powder diffraction (XRPD) pattern with characteristic peaks at 4.1±0.1° 2-Theta, 8.3±0.1° 2-Theta, 12.4±0.1° 2-Theta, 16.6±0.1° 2-Theta, 19.4±0.1° 2-Theta, 20.1±0.1° 2-Theta, 20.6±0.1° 2-Theta, 21.9±0.1° 2-Theta, 23.0±0.1° 2-Theta, 25.0±0.1° 2-Theta;

an X-ray powder diffraction (XRPD) pattern post storage at 40° C. and 75% RH for at least a week that is substantially the same as that observed for the crystalline Form 1 of (E)-3-(4-((E)-2-(2-chloro-4-fluorophenyl)-1-(1H-indazol-5-yl)but-1-en-1-yl)phenyl)acrylic acid, N-methyl glucamine salt;

a DSC thermogram with an endotherm having an onset temperature at about 121° C.;

a DSC thermogram substantially similar to the one set forth in FIG. 5;

a TGA thermogram with 3 weight loses observed between 40-102° C., 102-143° C., and 143-346° C. degradation;

A TGA thermogram substantially similar to the one set forth in FIG. 6; or combinations thereof.

In some embodiments, Pattern 2 has an X-Ray powder diffraction (XRPD) pattern substantially the same as shown in FIG. 4.

In some embodiments, Pattern 2 has an X-ray powder diffraction (XRPD) pattern with characteristic peaks at 4.1±0.1° 2-Theta, 8.3±0.1° 2-Theta, 12.4±0.1° 2-Theta, 16.6±0.1° 2-Theta, 19.4±0.1° 2-Theta, 20.1±0.1° 2-Theta, 20.6±0.1° 2-Theta, 21.9±0.1° 2-Theta, 23.0±0.1° 2-Theta, 25.0±0.1° 2-Theta.

In some embodiments, Pattern 2 has an X-ray powder diffraction (XRPD) pattern post storage at 40° C. and 75% RH for at least a week that is substantially the same as that observed for the crystalline Form 1 as claimed in claim 4.

In some embodiments, Pattern 2 has a DSC thermogram with an endotherm having an onset temperature at about 121° C.

In some embodiments, Pattern 2 has a DSC thermogram substantially similar to the one set forth in FIG. 5.

In some embodiments, Pattern 2 has a TGA thermogram with 3 weight loses observed between 40-102° C., 102-143° C., and 143-346° C. degradation.

In some embodiments, Pattern 2 has a TGA thermogram substantially similar to the one set forth in FIG. 6.

In some embodiments, Pattern 2 is characterized as having properties (a), (b), (c), (d), (e), (f), and (g).

In some embodiments, Pattern 2 was obtained from dimethylsulfoxide.

In some embodiments, Pattern 2 is a dimethylsulfoxide solvate.

Preparation of Crystalline Forms

In some embodiments, a crystalline form of a pharmaceutically acceptable salt of (E)-3-(4-((E)-2-(2-chloro-4-fluorophenyl)-1-(1H-indazol-5-yl)but-1-en-1-yl)phenyl) acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt) is prepared as outlined in the Examples. It is noted that solvents, temperatures and other reaction conditions presented herein may vary.

Suitable Solvents

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. Preferred solvents are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene.

Class 3 solvents, which possess low toxicity, include: acetic acid, acetone, anisole, 1-butanol, 2-butanol, butyl acetate, tert-butylmethyl ether (MTBE), cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran.

In some embodiments, compositions comprising a crystalline form of a pharmaceutically acceptable salt of (E)-3-(4-((E)-2-(2-chloro-4-fluorophenyl)-1-(1H-indazol-5-yl)but-1-en-1-yl)phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt) include a residual amount of an organic solvent(s). In some embodiments, compositions comprising a crystalline form of a pharmaceutically acceptable salt of (E)-3-(4-((E)-2-(2-chloro-4-fluorophenyl)-1-(1H-indazol-5-yl)but-1-en-1-yl)phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt) include a detectable amount of an organic solvent(s). In some embodiments, compositions comprising (a crystalline form of a pharmaceutically acceptable salt of (E)-3-(4-((E)-2-(2-chloro-4-fluorophenyl)-1-(1H-indazol-5-yl)but-1-en-1-yl)phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt) include a residual amount of a Class 3 solvent. In some embodiments, the organic solvent is a Class 3 solvent. In some embodiments, the Class 3 solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran. In some embodiments, the Class 3 solvent is ethanol.

The methods and compositions described herein include the use of a crystalline form of a pharmaceutically acceptable salt of (E)-3-(4-((E)-2-(2-chloro-4-fluorophenyl)-1-(1H-indazol-5-yl)but-1-en-1-yl)phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt). In addition, the crystalline forms of the pharmaceutically acceptable salt of (E)-3-(4-((E)-2-(2-chloro-4-fluorophenyl)-1-(1H-indazol-5-yl)but-1-en-1-yl)phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt) described herein can exist in unsolvated as well as solvated forms with pharmaceutically acceptable solvents such as water, ethanol, and the like.

Certain Terminology

The term "cancer" as used herein refers to an abnormal growth of cells which tend to proliferate in an uncontrolled way and, in some cases, to metastasize (spread).

The term "breast cancer" as used herein refers to histologically or cytologically confirmed adenocarcinoma of the breast.

The term "locally advanced breast cancer" refers to cancer that has spread from where it started in the breast to nearby tissue or lymph nodes, but not to other parts of the body.

The term "metastatic breast cancer" refers to cancer that has spread from the breast to other parts of the body, such as the bones, liver, lungs, or brain. Metastatic breast cancer is also referred to as stage IV breast cancer.

The term "continuous daily dosing schedule" refers to the administration of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, daily without any drug holidays. In some embodiments, a continuous daily dosing schedule comprises administration of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, every day at roughly the same time each day.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, delaying progression of condition, relieving a condition caused by the disease or condition, or stopping the symptoms of the disease or condition either prophylactically and/or therapeutically. In some embodiments, treatment includes extending progression-free survival. In some embodiments, treatment includes reducing the relative risk of disease progression compared to other treatment options. In some embodiments, other treatment options include but are not limited to hormonal treatments (e.g. antiestrogen therapy, such as tamoxifen and/or fulvestrant).

The term "progression-free survival" is the amount of time during and after the treatment of a disease, such as cancer, that a patient lives with the disease but it does not get worse. In a clinical trial, measuring progression-free survival is one way to see how well a treatment works.

The term "pharmaceutically acceptable excipient," as used herein, refers to a material, such as a carrier, diluent, stabilizer, dispersing agent, suspending agent, thickening agent, etc. which allows processing the active pharmaceutical ingredient (API) into a form suitable for administration to a mammal. In one aspect, the mammal is a human. Pharmaceutically acceptable excipients refer to materials which do not substantially abrogate the desired biological activity or desired properties of the compound (i.e. API), and is relatively nontoxic, i.e., the material is administered to an individual without causing undesirable biological effects or interacting in a deleterious manner with any of the components of the composition in which it is contained.

"Active pharmaceutical ingredient" or API refers to a compound that possesses a desired biological activity or desired properties. In some embodiments, an API is a crystalline form of a pharmaceutically acceptable salt of (E)-3-(4-((E)-2-(2-chloro-4-fluorophenyl)-1-(1H-indazol-5-yl)but-1-en-1-yl)phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt). In some embodiments, an API is crystalline (E)-3-(4-((E)-2-(2-Chloro-4-fluorophenyl)-1-(1H-indazol-5-yl)but-1-en-1-yl)phenyl)acrylic acid, N-methyl glucamine salt. In some embodiments, the API has a purity of greater than 90%, greater than 95%, greater than 96%, greater than 97%, greater than 98%, greater than 98%, or greater than 99%.

The term "pharmaceutical composition" refers to a mixture of a crystalline form of a pharmaceutically acceptable salt of (E)-3-(4-((E)-2-(2-chloro-4-fluorophenyl)-1-(1H-indazol-5-yl)but-1-en-1-yl)phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt), with other chemical components, such as carriers, stabilizers, diluents, dispersing agents, suspending agents, thickening agents, excipients, etc. The pharmaceutical composition facilitates administration of the compound to a mammal.

Administration of a combination of agents, as used herein, includes administration of the agents described in a single composition or in a combination therapy wherein one or more agent is administered separately from at least one other agent.

"Detectable amount" refers to an amount that is measurable using standard analytic methods (e.g. ion chromatography, mass spectrometry, NMR, HPLC, gas chromatography, elemental analysis, IR spectroscopy, inductively coupled plasma atomic emission spectrometry, USP<231>Method II, etc.) (ICH guidance, *Q2A Text on Validation of Analytical Procedures* (March 1995) and *Q2B Validation of Analytical Procedures: Methodology* (November 1996)).

The term "acceptable" with respect to a formulation, composition or ingredient, as used herein, means having no persistent detrimental effect on the general health of the subject being treated.

The terms "effective amount" or "therapeutically effective amount," as used herein, refer to a sufficient amount of an agent being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. The term "therapeutically effective amount" includes, for example, a prophylactically effective amount.

The effective amount will be selected based on the particular patient and the disease level. It is understood that "an effect amount" or "a therapeutically effective amount" varies from subject to subject, due to variation in metabolism of drug, age, weight, general condition of the subject, the condition being treated, the severity of the condition being treated, and the judgment of the prescribing physician. In one embodiment, an appropriate "effective" amount in any individual case is determined using techniques, such as a dose escalation study. In some embodiments, the term "effective amount" or "therapeutically effective amount," is used in reference to (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, and refers to a sufficient amount of (E)-3-(4-((E)-2-(2-chloro-4-fluorophenyl)-1-(1H-indazol-5-yl)but-1-en-1-yl)phenyl)acrylic acid, or a pharmaceutically acceptable salt thereof, being administered which will relieve to some extent one or more of the symptoms of the disease or condition being treated.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "kit" and "article of manufacture" are used as synonyms.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target. The term "subject" or "patient" encompasses mammals. In one aspect, the mammal is a human.

Pharmaceutical Compositions/Formulations

Pharmaceutical compositions are formulated in a conventional manner using one or more physiologically acceptable carriers comprising excipients and auxiliaries which facilitate processing of the active compounds into preparations which are used pharmaceutically. Suitable techniques, carriers, and excipients include those found within, for example, *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), herein incorporated by reference in their entirety.

In some embodiments, a crystalline form of a pharmaceutically acceptable salt of (E)-3-(4-((E)-2-(2-chloro-4-fluorophenyl)-1-(1H-indazol-5-yl)but-1-en-1-yl)phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt), is formulated for oral administration to a mammal. In some embodiments, a crystalline form of a pharmaceutically acceptable salt of (E)-3-(4-((E)-2-(2-chloro-4-fluorophenyl)-1-(1H-indazol-5-yl)but-1-en-1-yl)phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt), is formulated into an oral dosage form. In some embodiments, a crystalline form of a pharmaceutically acceptable salt of (E)-3-(4-((E)-2-(2- chloro-4-fluorophenyl)-1-(1H-indazol-5-yl)but-1-en-1-yl) phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt), is formulated into a solid oral dosage form. In some embodiments, a crystalline form of a pharmaceutically acceptable salt of (E)-3-(4-((E)-2-(2-chloro-4-fluorophenyl)-1-(1H-indazol-5-yl)but-1-en-1-yl) phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt), is formulated into a tablet, powder, pill, capsule, and the like, for oral ingestion by a mammal.

Contemplated pharmaceutical compositions provide a therapeutically effective amount of a crystalline form of a pharmaceutically acceptable salt of (E)-3-(4-((E)-2-(2-chloro-4-fluorophenyl)-1-(1H-indazol-5-yl)but-1-en-1-yl) phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt), enabling, for example, once-a-day, twice-a-day, three times a day, etc. administration. In one aspect, pharmaceutical compositions provide an effective amount of a crystalline form of a pharmaceutically acceptable salt of (E)-3-(4-((E)-2-(2-chloro-4-fluorophenyl)-1-(1H-indazol-5-yl)but-1-en-1-yl)phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt), enabling once-a-day dosing.

Dose Amounts

In certain embodiments, the amount of a crystalline form of a pharmaceutically acceptable salt of (E)-3-(4-((E)-2-(2-chloro-4-fluorophenyl)-1-(1H-indazol-5-yl)but-1-en-1-yl) phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt), in the pharmaceutical compositions is about 1 mg to about 1.5 g per dose, 1 mg to about 1 g per dose, or about 1 mg to about 1 g per dose.

In certain embodiments, the amount of a crystalline form of a pharmaceutically acceptable salt of (E)-3-(4-((E)-2-(2-chloro-4-fluorophenyl)-1-(1H-indazol-5-yl)but-1-en-1-yl) phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt), in the pharmaceutical compositions is about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, about 910 mg, about 920 mg, about 930 mg, about 940 mg, about 950 mg, about 960 mg, about 970 mg, about 980 mg, about 990 mg, or about 1000 mg.

In one embodiment, the desired dose is conveniently presented in a single dose or in divided doses administered simultaneously (or over a short period of time) or at appropriate intervals, for example as two, three, four or more sub-doses per day.

In one embodiment, the daily dosages appropriate for a crystalline form of a pharmaceutically acceptable salt of (E)-3-(4-((E)-2-(2-chloro-4-fluorophenyl)-1-(1H-indazol-5-yl)but-1-en-1-yl)phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt), is from about 0.01 to about 30 mg/kg per body weight. In other embodiments, the daily dosage or the amount of active in the dosage form are lower or higher than the ranges indicated herein.

Methods of Dosing and Treatment Regimens

In one embodiment, the pharmaceutical compositions described herein comprising a crystalline form of a pharmaceutically acceptable salt of (E)-3-(4-((E)-2-(2-chloro-4-fluorophenyl)-1-(1H-indazol-5-yl)but-1-en-1-yl)phenyl) acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt) are administered for prophylactic and/or therapeutic treatments. In therapeutic applications, the compositions are administered to a patient already suffering from a disease or condition, in an amount sufficient to cure or at least partially arrest at least one of the symptoms of the disease or condition. In certain embodiments, amounts effective for this use depend on the severity and course of the disease or condition, previous therapy, the patient's health status, weight, and response to the drugs, and/or the judgment of the treating physician.

In prophylactic applications, the pharmaceutical compositions described herein comprising a crystalline form of a pharmaceutically acceptable salt of (E)-3-(4-((E)-2-(2-chloro-4-fluorophenyl)-1-(1H-indazol-5-yl)but-1-en-1-yl) phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt) are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In certain embodiments, administration of the compound, compositions or therapies as described herein includes chronic administration. In certain embodiments, chronic administration includes administration for an extended period of time, including, e.g., throughout the duration of the patient's life in order to ameliorate or otherwise control or limit the symptoms of the patient's disease or condition. In some embodiments, chronic administration includes daily administration.

In some embodiments, administration of the compound, compositions or therapies described herein is given continuously. In alternative embodiments, the dose of drug being administered is temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday is from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but can nevertheless be determined according to the particular circumstances surrounding the case, including, e.g., the specific agent being administered, the route of administration, the condition being treated, and the subject or host being treated.

Combination Treatments

In certain instances, it is appropriate to administer a crystalline form of a pharmaceutically acceptable salt of (E)-3-(4-((E)-2-(2-chloro-4-fluorophenyl)-1-(1H-indazol-5-yl)but-1-en-1-yl)phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt), in combination with another therapeutic agent.

In one embodiment, the compositions and methods described herein are also used in conjunction with other therapeutic reagents that are selected for their particular usefulness against the condition that is being treated. In general, the compositions described herein and, in embodiments where combinational therapy is employed, other agents do not have to be administered in the same pharmaceutical composition, and are, because of different physical and chemical characteristics, administered by different routes. In one embodiment, the initial administration is made according to established protocols, and then, based upon the observed effects, the dosage, modes of administration and times of administration, further modified.

In various embodiments, a crystalline form of a pharmaceutically acceptable salt of (E)-3-(4-((E)-2-(2-chloro-4-fluorophenyl)-1-(1H-indazol-5-yl)but-1-en-1-yl)phenyl) acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt), is administered concurrently (e.g., simultaneously, essentially simultaneously or within the same treatment protocol) or sequentially, depending upon the nature of the disease and the condition of the patient. In certain embodiments, the determination of the order of administration, and the number of repetitions of administration of each therapeutic agent during a treatment protocol, is based upon evaluation of the disease being treated and the condition of the patient.

For combination therapies described herein, dosages of the co-administered compounds vary depending on the type of co-drug employed, on the specific drug employed, on the disease or condition being treated and so forth.

The individual compounds of such combinations are administered either sequentially or simultaneously in separate or combined pharmaceutical formulations. In one embodiment, the individual compounds will be administered simultaneously in a combined pharmaceutical formulation.

Appropriate doses of known therapeutic agents will be appreciated by those skilled in the art.

The combinations referred to herein are conveniently presented for use in the form of a pharmaceutical compositions together with a pharmaceutically acceptable diluent(s) or carrier(s).

Kits/Articles of Manufacture

For use in the therapeutic methods of use described herein, kits/articles of manufacture are also described herein. Such kits include a carrier, package, or container that is optionally compartmentalized to receive one or more doses of a pharmaceutical composition of a crystalline form of a pharmaceutically acceptable salt of (E)-3-(4-((E)-2-(2-chloro-4-fluorophenyl)-1-(1H-indazol-5-yl)but-1-en-1-yl) phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt), for use in a method described herein. The kits provided herein contain packaging materials. Packaging materials for use in packaging pharmaceutical products include, but are not limited to those described in e.g., U.S. Pat. No. 5,323,907. Examples of pharmaceutical packaging materials include, but are not limited to, blister packs, bottles, tubes, bags, containers, bottles, and any packaging material suitable for a selected formulation and intended mode of administration and treatment. A wide array of formulations of a crystalline form of a pharmaceutically acceptable salt of (E)-3-(4-((E)-2-(2-chloro-4-fluorophenyl)-1-(1H-indazol-5-yl)but-1-en-1-yl) phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt), and compositions thereof are contemplated as are a variety of treatments for any disease, disorder, or condition that would benefit by treatment with an ER modulator.

For example, the container(s) include a crystalline form of a pharmaceutically acceptable salt of (E)-3-(4-((E)-2-(2-chloro-4-fluorophenyl)-1-(1H-indazol-5-yl)but-1-en-1-yl) phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt), optionally in a composition or in combination with another agent as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a crystalline form of a pharmaceutically acceptable salt of (E)-3-(4-((E)-2-(2-chloro-4-fluorophenyl)-1-(1H-indazol-5-yl)but-1-en-1-yl)phenyl)acrylic acid (e.g. (E)-3-(4-((E)-2-(2-chloro-4-fluorophenyl)-1-(1H-indazol-5-yl)but-1-en-1-yl)phenyl)acrylic acid, N-methyl glucamine salt), formulated in a compatible pharmaceutical carrier are also prepared, placed in an appropriate container, and labeled for treatment of an indicated condition.

EXAMPLES

Example 1

Salt Forms of (E)-3-(4-((E)-2-(2-chloro-4-fluorophenyl)-1-(1H-indazol-5-yl)but-1-en-1-yl)phenyl)acrylic acid (E)-3-(4-((E)-2-(2-Chloro-4-fluorophenyl)-1-(1H-indazol-5-yl)but-1-en-1-yl)phenyl)acrylic acid (ca. 50 mg) was weighed into 48×4 mL scintillation vials. 12 samples were then dissolved in a minimum amount of 1 of 4 solvents at 50° C. (ethyl acetate (EtOAc), dioxane and isopropyl alcohol (IPA)) or 65° C. (for acetonitrile (MeCN)). The samples were then shaken for 30 minutes at 50° C. or 65° C. to effect complete dissolution of the free acid prior to the addition of 1.1 eq of 1 of 12 stock base solutions or neat bases to each of the vials. The samples were then matured overnight prior to visual inspection then cooled to 5° C. for 6 hours. Any clear solutions were evaporated at RT until a precipitate had formed. Where no solid were observed on evaporation anti-solvent was added to the samples which were then matured (RT-50° C. on an 8 hour cycle for 7 days) prior to filtration in vacuo.

Selected bases included potassium hydroxide (4M aqueous solution), sodium hydroxide (4M aqueous solution), L-arginine (2M aqueous solution), calcium hydroxide, magnesium hydroxide, choline, L-Lysine monohydrate (2M aqueous solution), ethylenediamine, hydroxyethylpyrrolidine, ammonium hydroxide, N-methyl glucamine (2M aqueous solution), and tromethamine (2 M aqueous solution).

A number of stable, crystalline salts of (E)-3-(4-((E)-2-(2-chloro-4-fluorophenyl)-1-(1H-indazol-5-yl)but-1-en-1-yl)phenyl)acrylic acid were prepared. Most salts demonstrated solubility <1 mg/mL. Salts that exhibited higher aqueous solubility included choline, potassium, and N-methylglucamine salts. A summary of the crystallinities and solubilities of some of the prepared salts forms of (E)-3-(4-((E)-2-(2-chloro-4-fluorophenyl)-1-(1H-indazol-5-yl)but-1-en-1-yl)phenyl)acrylic acid is provided in the following table:

TABLE 1

Crystallinities and Solubilities of Prepared Salt Forms of (E)-3-(4-((E)-2-(2-chloro-4-fluorophenyl)-1-(1H-indazol-5-yl)but-1-en-1-yl)phenyl)acrylic acid

| Counterion | Solvent | Crystalline | Solubility (mg/mL) |
|---|---|---|---|
| Choline | Dioxane (5 Vols) | Yes | 8.57 |
| Choline | Ethyl Acetate (10 Vols) | Yes | 9.32 |
| Ethylenediamine | Ethyl Acetate (10 Vols) | Yes | 0.91 |
| Hydroxyethyl-pyrrolidine | Ethyl Acetate (10 Vols) | Yes | <0.0001 |
| Tromethamine | Ethyl Acetate (10 Vols) | Yes | 0.24 |
| Calcium hydroxide | IPA (5 Vols) | Yes | 0.002 |
| Magnesium hydroxide | IPA (5 Vols) | Yes | 0.75 |
| Potassium hydroxide | MeCN (300 Vols) | Yes | 10.17 |
| L-Arginine | MeCN (300 Vols) | Yes | 0.8 |
| Choline | MeCN (300 Vols) | Yes | 9.21 |
| Ethylenediamine | MeCN (300 Vols) | Yes | 0.21 |
| N-Methylglucamine | MeCN (300 Vols) | Yes | 10.63 |
| Tromethamine | MeCN (300 Vols) | Yes | 0.82 |

Example 2

Preparation of the NMG Salt of (E)-3-(4-((E)-2-(2-chloro-4-fluorophenyl)-1-(1H-indazol-5-yl)but-1-en-1-yl)phenyl)acrylic acid

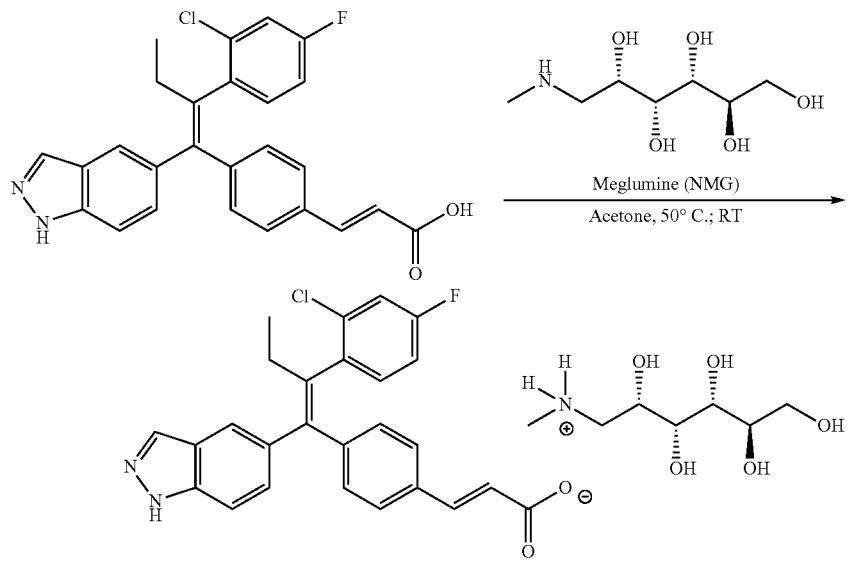

(E)-3-(4-((E)-2-(2-Chloro-4-fluorophenyl)-1-(1H-indazol-5-yl)but-1-en-1-yl)phenyl)acrylic acid (50.0 g, 111.9 mmol) and acetone (560 mL, HPLC grade) were charged to a 2 L 3-neck round bottom flask equipped with a mechanical stirrer, a reflux condenser, internal thermometer, and $N_2$ inlet at room temperature. The resulting pale yellow solution was vigorously stirred and heated to 50° C. (internal temperature) in a water bath. N-Methylglucamine (also known as N-methyl-D-glucamine, NMG, meglumine or (2R,3R,4R,5S)-6-(methylamino)hexane-1,2,3,4,5-pentol) (37.3 mL of a 3M aqueous solution, 111.9 mmol) was added dropwise via a syringe over 10 min to the reaction mixture at 50° C. resulting in the formation of a suspension with an oily residue noted the side of the flask. The suspension was vigorously stirred for 30 minutes at 50° C. prior to slowly cooling to room temperature with agitation over 2 hours. The suspension was stirred at room temperature for 16 h. The reaction mixture was filtered, collected solid washed with acetone (100 mL, HPLC grade) and dried under vacuum to afford the (E)-3-(4-0)-2-(2-chloro-4-fluorophenyl)-1-(1H-indazol-5-yl)but-1-en-1-yl)phenyl)acrylic acid, N-methyl glucamine salt as an off-white solid (65.1 g, 91%).

In an alternative embodiment, (E)-3-(4-((E)-2-(2-chloro-4-fluorophenyl)-1-(1H-indazol-5-yl)but-1-en-1-yl)phenyl)acrylic acid (1.0eq) was dissolved in 4.5 volumes of methanol total at 60° C. N-methyl-D-glucamine (1.3eq) was dissolved in 1.5 volumes of purified water at 50° C. Half of the N-methyl-D-glucamine solution was then added to the solution of (E)-3-(4-((E)-2-(2-chloro-4-fluorophenyl)-1-(1H-indazol-5-yl)but-1-en-1-yl)phenyl)acrylic acid in methanol at 60° C., and the mixture seeded with previously isolated (E)-3-(4-((E)-2-(2-chloro-4-fluorophenyl)-1-(1H-indazol-5-yl)but-1-en-1-yl)phenyl)acrylic acid N-methyl glucamine salt (form 1). The rest of the N-methyl-D-glucamine solution was then added over 60 minutes at 60° C. The reaction mixture was then stirred for at least an additional 60 minutes maintaining an internal temperature of 50° C., and then cooled over at least 8 hours to an internal temperature of 10° C. The mixture was then stirred for at least a further 1 hour. The suspension was then filtered off, the isolated solid washed with 10° C. methanol (2x 2v), and the solid dried at 120° C. until methanol content was ≤3000 ppm.

Example 3

Preparation of Amorphous (E)-3-(4-((E)-2-(2-chloro-4-fluorophenyl)-1-(1H-indazol-5-yl)but-1-en-1-yl)phenyl)acrylic acid, N-methyl glucamine salt Amorphous (E)-3-(4-((E)-2-(2-chloro-4-fluorophenyl)-1-(1H-indazol-5-yl)but-1-en-1-yl)phenyl)acrylic acid, N-methyl glucamine salt was prepared by lyophilizing (E)-3-(4-((E)-2-(2-chloro-4-fluorophenyl)-1-(1H-indazol-5-yl)but-1-en-1-yl)phenyl)acrylic acid, N-methyl glucamine salt from water. The resulting material was observed to be a white solid that was confirmed to be amorphous by XRPD analysis.

Example 4

Preparation of Crystalline Forms of (E)-3-(4-((E)-2-(2-chloro-4-fluorophenyl)-1-(1H-indazol-5-yl)but-1-en-1-yl)phenyl)acrylic acid, N-methyl glucamine salt Form 1
Maturation
(E)-3-(4-((E)-2-(2-chloro-4-fluorophenyl)-1-(1H-indazol-5-yl)but-1-en-1-yl)phenyl)acrylic acid, N-methyl glucamine salt (ca. 25 mg) was weighed into 1.5 mL vials. An appropriate amount of solvent (500 μL) was then added to create a suspension at room temperature. Appropriate solvents included of 1,4 dioxane, toluene, tert-butylmethyl ether (TBME), tetralin, anisole, butyl acetate, ethyl acetate, isopropyl acetate, isopropyl alcohol (IPA), 1,2-dimethoxyethane (DME), diclormethane (DCM), methyl isobutyl ketone (MIBK), methyl ethyl ketone (MEK), acetone, methanol, ethanol, acetonitrile, and nitromethane. Additionally, MIBK, methanol, and acetonitrile with 5% water were used in further instances. The resulting slurry was then placed in a platform shaker incubator (Heidolph Titramax/Inkubator 1000) and subjected to a series of heat-cool cycles under shaking from room temperature to 50° C. (8 hour cycles: heating to 50° C. for 4 hours and then cooling to room temperature for a further 4 hours) for up to 7 days to obtain a crystalline solid. The resulting solids were confirmed to be Form 1 of (E)-3-(4-((E)-2-(2-chloro-4-fluorophenyl)-1-(1H-indazol-5-yl)but-1-en-1-yl)phenyl)acrylic acid, N-methyl glucamine salt by XRPD analysis.

In other embodiments, amorphous (E)-3-(4-((E)-2-(2-chloro-4-fluorophenyl)-1-(1H-indazol-5-yl)but-1-en-1-yl)phenyl)acrylic acid, N-methyl glucamine salt (ca. 25 mg) was weighed into 1.5 mL vials. 500 μl of THF (with or without 5% water was added. The resulting slurry was then placed in a platform shaker incubator (Heidolph Titramax/Inkubator 1000) and subjected to a series of heat-cool cycles under shaking from RT to 50° C. (8 hour cycles: heating to 50° C. for 4 hours and then cooling to RT for a further 4 hours) for up to 7 days to obtain an oil. 250 μl of anti-solvent (heptanes was added) and the solution was subjected to another series of heat-cool cycles under shaking from RT to 50° C. (8 hour cycles: heating to 50° C. for 4 hours and then cooling to RT for a further 4 hours) for 7 days. The resulting solid was confirmed to be Form 1 of (E)-3-(4-((E)-2-(2-chloro-4-fluorophenyl)-1-(1H-indazol-5-yl)but-1-en-1-yl)phenyl)acrylic acid, N-methyl glucamine salt by XRPD analysis.

Slow Evaporation

Amorphous (E)-3-(4-((E)-2-(2-chloro-4-fluorophenyl)-1-(1H-indazol-5-yl)but-1-en-1-yl)phenyl)acrylic acid, N-methyl glucamine salt (ca. 25 mg) was dissolved with 500 μl of methanol (with or without 5% water) or 1500 μL acetonitrile. The solution was slowly evaporated at RT to provide to provide a crystalline solid, which was confirmed to be Form 1 of (E)-3-(4-((E)-2-(2-chloro-4-fluorophenyl)-1-(1H-indazol-5-yl)but-1-en-1-yl)phenyl)acrylic acid, N-methyl glucamine salt by XRPD analysis.

In some embodiments, amorphous (E)-3-(4-((E)-2-(2-chloro-4-fluorophenyl)-1-(1H-indazol-5-yl)but-1-en-1-yl)phenyl)acrylic acid, N-methyl glucamine salt (ca. 25 mg) was dissolved with 500 μL of THF or 1,4-dioxane (with 5% water). The solution was slowly evaporated at RT to provide to provide an oil. 250 μl of anti-solvent (heptanes) was then added and then subjected to a maturation cycle for up to 7 days. The maturation cycle consisted of 8 hour cycles: heating to 50° C. for 4 hours and then cooling to RT for a further 4 hours. A crystalline solid was obtained and the resulting solid was confirmed to be Form 1 of (E)-3-(4-((E)-2-(2-chloro-4-fluorophenyl)-1-(1H-indazol-5-yl)but-1-en-1-yl)phenyl)acrylic acid, N-methyl glucamine salt by XRPD analysis.

Cooling

A super saturated solution of amorphous (E)-3-(4-((E)-2-(2-chloro-4-fluorophenyl)-1-(1H-indazol-5-yl)but-1-en-1-yl)phenyl)acrylic acid, N-methyl glucamine salt was prepared by heating the (E)-3-(4-((E)-2-(2-Chloro-4-fluorophenyl)-1-(1H-indazol-5-yl)but-1-en-1-yl)phenyl)acrylic acid, N-methyl glucamine salt in methanol (100 μL) to 65° C. Hot filtering was implemented if necessary to provide a clear solution. The solution was then subjected to an initial cooling period of 16 hours at 4° C. followed overnight cooling at −20° C. If no solid was observed, then 10 µL of an anti-solvent, such as heptanes, was then added and the solution was further cooled at −20° C. for an additional 24 hours. The resulting solid obtained was confirmed to be Form 1 of (E)-3-(4-((E)-2-(2-Chloro-4-fluorophenyl)-1-(1H-indazol-5-yl)but-1-en-1-yl)phenyl)acrylic acid, N-methyl glucamine salt by XRPD analysis.

Form 1 is also prepared by the procedure described in Example 2.

At 75% relative humidity at 40° C. or 96% relative humidity at 25° C. for 7 days, Form 1 showed no visible change by XRPD analysis.

Pattern 2

Amorphous (E)-3-(4-((E)-2-(2-chloro-4-fluorophenyl)-1-(1H-indazol-5-yl)but-1-en-1-yl)phenyl)acrylic acid, N-methyl glucamine salt (ca. 25 mg) was dissolved with 100 µL of DMSO (with or without 5% water). The solution was slowly evaporated at RT to provide an oil. 250 µL of anti-solvent (heptane) was then added and then subjected to a maturation cycle for up to 7 days. The maturation cycle consisted of 8 hour cycles: heating to 50° C. for 4 hours and then cooling to RT for a further 4 hours. A crystalline solid was obtained and the resulting solid was confirmed to be Pattern 2 of (E)-3-(4-((E)-2-(2-chloro-4-fluorophenyl)-1-(1H-indazol-5-yl)but-1-en-1-yl)phenyl)acrylic acid, N-methyl glucamine salt by XRPD analysis.

In some embodiments, approximately 1.5 g of (E)-3-(4-((E)-2-(2-chloro-4-fluorophenyl)-1-(1H-indazol-5-yl)but-1-en-1-yl)phenyl)acrylic acid, N-methyl glucamine salt was lyophilized from 30 mL of water to yield the amorphous (E)-3-(4-((E)-2-(2-chloro-4-fluorophenyl)-1-(1H-indazol-5-yl)but-1-en-1-yl)phenyl)acrylic acid, N-methyl glucamine salt. To the amorphous (E)-3-(4-((E)-2-(2-chloro-4-fluorophenyl)-1-(1H-indazol-5-yl)but-1-en-1-yl)phenyl)acrylic acid, N-methyl glucamine salt was added 20 mL of heptane (anti-solvent) and 100 µL of dimethylsulfoxide (DMSO). The resulting slurry was then placed in a platform shaker incubator (Heidolph Titramax/Inkubator 1000) and subjected to a series of heat-cool cycles under shaking from room temperature to 50° C. (8 hour cycles: heating to 50° C. for 4 hours and then cooling to room temperature for a further 4 hours) for 7 days. The resulting solid was confirmed to be Pattern 2 of (E)-3-(4-((E)-2-(2-chloro-4-fluorophenyl)-1-(1H-indazol-5-yl)but-1-en-1-yl)phenyl)acrylic acid, N-methyl glucamine salt by XRPD analysis.

Subsequent studies confirmed that Pattern 2 is a DMSO solvate. $^1$H NMR analysis confirmed the presence of DMSO in Pattern 2 of (E)-3-(4-((E)-2-(2-chloro-4-fluorophenyl)-1-(1H-indazol-5-yl)but-1-en-1-yl)phenyl)acrylic acid, N-methyl glucamine salt. When Pattern 2 was heated to 110° C. for 10 min and re-analyzed by $^1$H NMR, 0.7 eq of DMSO was still present. After storage at 40° C./75% RH for 7 days, XRPD analysis showed that Pattern 2 had converted to Form 1, and subsequent $^1$H NMR analysis confirmed that DMSO was no longer present.

Example 5

X-Ray Powder Diffraction (XRPD)

X-Ray powder diffraction patterns were collected on a Bruker AXS C2 GADDS or a Bruker AXS D8 Advance diffractometer.

Bruker AXS C2 GADDS: X-Ray Powder Diffraction patterns were collected on a Bruker AXS C2 GADDS diffractometer using Cu Ka radiation (40 kV, 40 mA), automated XYZ stage, laser video microscope for auto-sample positioning and a HiStar 2-dimensional area detector. X-ray optics consists of a single Gael multilayer mirror coupled with a pinhole collimator of 0.3 mm. The beam divergence, i.e. the effective size of the X-ray beam on the sample, was approximately 4 mm. A θ-θ continuous scan mode was employed with a sample detector distance of 20 cm which gives an effective 2θ range of 3.2° 29.7°. Typically the sample would be exposed to the X-ray beam for 120 seconds. The software used for data collection was GADDS for WNT 4.1.16 and the data were analyzed and presented using Diffrac Plus EVA v 11.0.0.2 or v13.0.0.2.

Samples run under ambient conditions were prepared as flat plate specimens using powder as received without grinding. Approximately 1-2 mg of the sample was lightly pressed on a glass slide to obtain a flat surface.

Samples run under non-ambient conditions were mounted on a silicon wafer with heat-conducting compound. The sample was then heated to the appropriate temperature at ca.10° C./min$^{-1}$ and subsequently held isothermally for 2 minutes before data collection was initiated.

Bruker AXS D8 Advance: X-Ray Powder Diffraction patterns were collected on a Bruker D8 diffractometer using Cu Ka radiation (40 kV, 40 mA), θ-2θ goniometer, and divergence of V4 and receiving slits, a Ge monochromator and a Lynxeye detector. The instrument is performance checked using a certified Corundum standard (NIST 1976). The software used for data collection was Diffrac Plus XRD Commander v2.5.0 and the data were analyzed and presented using Diffrac Plus EVA v 11.0.0.2 or v 13.0.0.2. Samples were run under ambient conditions as flat plate specimens using powder. The sample was gently packed into a cavity cut into polished, zero-background (510) silicon wafer. The sample was rotated in its own plane during analysis. The details of the data collection are:

Angular range: 2 to 42 °2θ
Step size: 0.05 °2θ
Collection time: 0.5 s.step$^{-1}$ Form 1

The X-Ray powder diffraction pattern for Form 1 of (E)-3-(4-((E)-2-(2-chloro-4-fluorophenyl)-1-(1H-indazol-5-yl)but-1-en-1-yl)phenyl)acrylic acid, N-methyl glucamine salt is displayed in FIG. 1. Characteristic peaks include 4.7±0.1° 2-Theta, 9.4±0.1° 2-Theta, 12.3±0.1° 2-Theta, 14.1±0.1° 2-Theta, 17.3±0.1° 2-Theta, 18.7±0.1° 2-Theta, 19.9±0.1° 2-Theta, 20.2±0.1° 2-Theta, 21.5±0.1° 2-Theta, 24.3±0.1° 2-Theta, 24.7±0.1° 2-Theta.

Pattern 2

The X-Ray powder diffraction pattern for Pattern 2 of (E)-3-(4-((E)-2-(2-chloro-4-fluorophenyl)-1-(1H-indazol-5-yl)but-1-en-1-yl)phenyl)acrylic acid, N-methyl glucamine salt is displayed in FIG. 4. Characteristic peaks include 4.1±0.1° 2-Theta, 8.3±0.1° 2-Theta, 12.4±0.1° 2-Theta, 16.6±0.1° 2-Theta, 19.4±0.1° 2-Theta, 20.1±0.1° 2-Theta, 20.6±0.1° 2-Theta, 21.9±0.1° 2-Theta, 23.0±0.1° 2-Theta, 25.0±0.1° 2-Theta.

Example 6

Differential Scanning Calorimetry (DSC) and Thermogravimetric Analysis (TGA)

DSC data were collected on a TA Instruments Q2000 equipped with a 50 position auto-sampler. The calibration for thermal capacity was carried out using sapphire and the calibration for energy and temperature was carried out using certified indium. Typically 0.5-3 mg of each sample, in a pin-holed aluminum pan, was heated at 10° C./min from 25° C. to 275° C. A purge of dry nitrogen at 50 mL/min was maintained over the sample. Modulated temperature DSC was carried out using an underlying heating rate of 2° C./min and temperature modulation parameters of ±0.318° C. (amplitude) every 60 seconds (period). The instrument control software was Advantage for Q Series v2.8.0.392 and Thermal Advantage v4.8.3 and the data were analyzed using Universal Analysis v4.4A.

TGA data were collected on a TA Instruments Q500 TGA, equipped with a 16 position auto-sampler. The instrument was temperature calibrated using certified Alumel and Nickel. Typically 5-10 mg of each sample was loaded onto a pre-tared aluminum DSC pan and heated at 10° C./min from ambient temperature to 350° C. A nitrogen purge at 60 mL/min was maintained over the sample. The instrument control software was Advantage for Q Series v2.8.0.392 and Thermal Advantage v4.8.3 and the data were analyzed using Universal Analysis v4.4A.

Form 1

A sample of Form 1 of (E)-3-(4-((E)-2-(2-chloro-4-fluorophenyl)-1-(1H-indazol-5-yl)but-1-en-1-yl)phenyl)acrylic acid, N-methyl glucamine salt was analyzed by DSC and TGA, and the thermograms are shown in FIG. 2 and FIG. 3 respectively. DSC analysis of Form 1 showed an endotherm having an onset at about 149° C. (melt). TGA analysis showed a single weight loss of 2.2% w/w before decomposition. In some embodiments, static stability experiments showed that upon extended storage in high humidity conditions at 40° C., no visible change was observed by XRPD.

Pattern 2

Pattern 2 of (E)-3-(4-((E)-2-(2-chloro-4-fluorophenyl)-1-(1H-indazol-5-yl)but-1-en-1-yl)phenyl)acrylic acid, N-methyl glucamine salt is a DMSO solvate. A sample of Pattern 2 was analyzed by DSC and TGA, and the thermograms are shown in FIG. 5 and FIG. 6 respectively. TGA analysis showed a single weight loss of 3.1% w/w which was associated with an endotherm at 121° C. (melt) observed by DSC.

Example 7

Gravimetric Vapor Sorption (GVS)

Sorption isotherms were obtained using a SMS DVS Intrinsic moisture sorption analyzer, controlled by DVS Intrinsic Control software v1.0.0.30. The sample temperature was maintained at 25° C. by the instrument controls. The humidity was controlled by mixing streams of dry and wet nitrogen, with a total flow rate of 200 mL/min. The relative humidity was measured by a calibrated Rotronic probe (dynamic range of 1.0-100% RH), located near the sample. The weight change, (mass relaxation) of the sample as a function of % RH was constantly monitored by the microbalance (accuracy+0.005 mg).

Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0-90% RH range. Data analysis was undertaken in Microsoft Excel using DVS Analysis Suite v6.0.0.7.

TABLE 2

Method Parameters for SMS DVS Intrinsic Experiments

| Parameters | Values |
|---|---|
| Adsorption - Scan 1 | 40-90% RH |
| Desorption/Adsorption - Scan 2 | 90-0, 0-40% RH |
| Intervals (% RH) | 10 |
| Number of Scans | 2 |
| Flow rate (ml · min$^{-1}$) | 200 |
| Temperature (° C.) | 25 |
| Stability (° C. · min$^{-1}$) | 0.2 |
| Sorption Time (hours) | 6 hour time out |

The sample was recovered after completion of the isotherm and re-analyzed by XRPD.

Form 1

The GVS analysis of Form 1 of (E)-3-(4-((E)-2-(2-chloro-4-fluorophenyl)-1-(1H-indazol-5-yl)but-1-en-1-yl)phenyl) acrylic acid, N-methyl glucamine salt showed ca. 4.75% mass uptake between 0-90% RH with no hysteresis and rate of water uptake was observed to increase at >80% RH. No change in the XRPD pattern of the material after GVS analysis was observed suggesting that Form 1 was stable under the GVS conditions.

No difference in the XRPD patterns of Form 1 before and after storage at 25° C. and 96% RH for 7 days was observed. Furthermore, no difference in the XRPD patterns of Form 1 before and after storage at 40° C. and 75% RH for 7 days. These results suggest that Form 1 was stable under these conditions.

Example 8

Water Determination by Karl Fischer Titration (KF)

The water content of each sample was measured on a Metrohm 874 Oven Sample Processor at 150° C. with 851 Titrano Coulometer using Hydranal Coulomat AG oven reagent and nitrogen purge. Weighed solid samples were introduced into a sealed sample vial. Approximately 10 mg of sample was used per titration and duplicate determinations were made.

In some embodiments, the water content for Form 1 of (E)-3-(4-((E)-2-(2-chloro-4-fluorophenyl)-1-(1H-indazol-5-yl)but-1-en-1-yl)phenyl)acrylic acid, N-methyl glucamine salt was observed to be 2.2% (w/w).

Example 9

Thermodynamic Aqueous Solubility

Aqueous solubility was determined by suspending sufficient compound in water to give a maximum final concentration of ≥10 mg/mL of the parent free-form of the compound. The suspension was equilibrated at 25° C. for 24 hours then the pH was measured. The suspension was then filtered through a glass fibre C filter. The filtrate was then diluted by an appropriate factor e.g. 101. Quantitation was by HPLC with reference to a standard solution of approximately 0.25 mg/mL in DMSO. Different volumes of the standard, diluted and undiluted sample solutions were injected. The solubility was calculated using the peak areas determined by integration of the peak found at the same retention time as the principal peak in the standard injection.

TABLE 3

HPLC Method Parameters for Solubility Measurements

| | |
|---|---|
| Type of method: | Reverse phase with gradient elution |
| Column: | Phenomenex Luna, C18 (2) 5 µm, 50 × 4.6 mm |
| Column Temperature (° C.): | 25 |
| Standard Injections (µl): | 1, 2, 3, 5, 7, 10 |
| Test Injections (µl): | 1, 2, 3, 10, 20, 50 |
| Detection: | 260, 80 |
| Wavelength, Bandwidth (nm): | |
| Flow Rate (mL/min): | 2 |
| Phase A: | 0.1% TFA in water |
| Phase B: | 0.085% TFA in acetonitrile |
| Timetable: | Time (min) / % Phase A / % Phase B |

| Time (min) | % Phase A | % Phase B |
|---|---|---|
| 0.0 | 95 | 5 |
| 1.0 | 80 | 20 |
| 2.3 | 5 | 95 |
| 3.3 | 5 | 95 |
| 3.5 | 95 | 5 |
| 4.4 | 95 | 5 |

Analysis was performed on an Agilent HP1100 series system equipped with a diode array detector and using ChemStation software vB.02.01-SR1.

A saturated aqueous solution of Form 1 of (E)-3-(4-((E)-2-(2-chloro-4-fluorophenyl)-1-(1H-indazol-5-yl)but-1-en-1-yl)phenyl)acrylic acid, N-methyl glucamine salt was observed to have an aqueous solubility of 15.77 mg/mL with a pH of about 5.45.

Example 10

Chemical Purity Determination

Purity analysis was performed on an Agilent HP1100 series system equipped with a diode array detector and using ChemStation software vB.02.01-SR1 using the method detailed below:

TABLE 4

HPLC Method Parameters for Chemical Purity Determinations

| | |
|---|---|
| Sample Preparation: | 0.5 mg/ml in acetonitrile:water 1:1 (unless otherwise stated) |
| Column: | Supelco Ascentis Express C18, 100 × 4.6 mm, 2.7 µm |
| Column Temperature (° C.): | 25 |
| Injection (µl): | 5 (unless otherwise stated) |
| Detection: | 255, 90 |
| Wavelength, Bandwidth (nm): | |
| Flow Rate (mL/min): | 2.0 |
| Phase A: | 0.1% TFA in water |
| Phase B: | 0.085% TFA in acetonitrile |
| Timetable: | Time (min) / % Phase A / % Phase B |

| Time (min) | % Phase A | % Phase B |
|---|---|---|
| 0 | 95 | 5 |
| 6 | 5 | 95 |
| 6.2 | 95 | 5 |
| 8 | 95 | 5 |

Samples of (E)-3-(4-((E)-2-(2-chloro-4-fluorophenyl)-1-(1H-indazol-5-yl)but-1-en-1-yl)phenyl)acrylic acid, N-methyl glucamine salt were found to be greater than 95% pure. In some embodiments, samples of (E)-3-(4-((E)-2-(2-chloro-4-fluorophenyl)-1-(1H-indazol-5-yl)but-1-en-1-yl)phenyl)acrylic acid, N-methyl glucamine salt were found to be greater than 95% pure, greater than 96% pure, greater than 97% pure, greater than 98% pure, or greater than 99% pure.

Example 11

Pharmaceutical Composition

Capsule Formulation

In one embodiment, capsule formulations of crystalline (E)-3-(4-((E)-2-(2-chloro-4-fluorophenyl)-1-(1H-indazol-5-yl)but-1-en-1-yl)phenyl)acrylic acid, N-methyl glucamine salt for administration to humans are prepared with the following ingredients:

TABLE 5

Components of Capsule Formulation

| Component | Function | Quantity per Size 4 Capsule | Quantity per Size 1 Capsule |
|---|---|---|---|
| crystalline (E)-3-(4-((E)-2-(2-chloro-4-fluorophenyl)-1-(1H-indazol-5-yl)but-1-en-1-yl)phenyl)acrylic acid, N-methyl glucamine salt | Active | 5 to 100 mg | 50 to 500 mg |
| Hypromellose, USP | Capsule Shell | 1 capsule | 1 capsule |

The process to prepare crystalline (E)-3-(4-((E)-2-(2-chloro-4-fluorophenyl)-1-(1H-indazol-5-yl)but-1-en-1-yl)phenyl)acrylic acid, N-methyl glucamine salt in a capsule is as follows: Weigh the required amount of (E)-3-(4-((E)-2-(2-chloro-4-fluorophenyl)-1-(1H-indazol-5-yl)but-1-en-1-yl)phenyl)acrylic acid, N-methyl glucamine salt, add into the appropriate size capsule, and close capsule.

The examples and embodiments described herein are illustrative and various modifications or changes suggested to persons skilled in the art are to be included within this disclosure. As will be appreciated by those skilled in the art, the specific components listed in the above examples may be replaced with other functionally equivalent components, e.g., diluents, binders, lubricants, fillers, and the like.

What is claimed is:

1. A crystalline Form 1 of (E)-3-(4-((E)-2-(2-chloro-4-fluorophenyl)-1-(1H-indazol-5-yl)but-1-en-1-yl)phenyl)acrylic acid, N-methyl glucamine salt that is characterized as having:
   (a) an X-Ray powder diffraction (XRPD) pattern substantially the same as shown in FIG. 1;
   (b) an X-ray powder diffraction (XRPD) pattern with characteristic peaks at 4.7±0.1° 2-Theta, 9.4±0.1° 2-Theta, 12.3±0.1° 2-Theta, 14.1±0.1° 2-Theta, 17.3±0.1° 2-Theta, 18.7±0.1° 2-Theta, 19.9±0.1° 2-Theta, 20.2±0.1° 2-Theta, 21.5±0.1° 2-Theta, 24.3±0.1° 2-Theta, 24.7±0.1° 2-Theta;
   (c) a DSC thermogram with an endotherm having an onset temperature at about 149° C.;
   (d) a DSC thermogram substantially similar to the one set forth in FIG. 2;
   (e) A TGA thermogram with 2 weight loses observed between 30-86° C., water loss and 199-346° C. degradation;
   (f) A TGA thermogram substantially similar to the one set forth in FIG. 3; or
   (g) combinations thereof.

2. The crystalline form of claim 1, wherein the crystalline form has an X-Ray powder diffraction (XRPD) pattern substantially the same as shown in FIG. 1.

3. The crystalline form of claim 1, wherein the crystalline form has an X-ray powder diffraction (XRPD) pattern with characteristic peaks at 4.7±0.1° 2-Theta, 12.2±0.1° 2-Theta, 14.1±0.1° 2-Theta, 17.2±0.1° 2-Theta, 19.8±0.1° 2-Theta, 20.1±0.1° 2Theta, 21.5±0.1° 2-Theta, 24.7±0.1° 2-Theta.

4. The crystalline form of claim 1, wherein the crystalline form has substantially the same X-ray powder diffraction (XRPD) pattern post storage at 40° C. and 75% RH for at least a week.

5. The crystalline form of claim 1, wherein the crystalline form has substantially the same X-ray powder diffraction (XRPD) pattern post storage at 25° C. and 96% RH for at least a week.

6. The crystalline form of claim 1, wherein the crystalline form has a DSC thermogram with an endotherm having an onset temperature at about 149° C.

7. The crystalline form of claim 1, wherein the crystalline form has a DSC thermogram substantially similar to the one set forth in FIG. 2.

8. The crystalline form of claim 1, wherein the crystalline form has a TGA thermogram with 2 weight loses observed between 30-86° C., water loss and 199-346° C. degradation.

9. The crystalline form of claim 1, wherein the crystalline form has a TGA thermogram substantially similar to the one set forth in FIG. 3.

10. The crystalline form of claim 1, wherein the crystalline form has an observed aqueous solubility that is greater than 10 mg/mL.

11. The crystalline form of claim 1, wherein the crystalline form is characterized as having properties (a), (b), (c), (d), (e), (f), and (g).

12. The crystalline form of claim 1, wherein the crystalline form was obtained from 1,4dioxane, toluene, tert-butylmethyl ether (TBME), tetralin, anisole, butyl acetate, ethyl acetate, isopropyl acetate, isopropyl alcohol (IPA), 1,2-dimethoxyethane (DME), dichloromethane (DCM), methyl isobutyl ketone (MIBK), methyl ethyl ketone (MEK), acetone, methanol, ethanol, acetonitrile, or nitromethane, or a combination thereof.

13. A crystalline form of (E)-3-(4-((E)-2-(2-chloro-4-fluorophenyl)-1-(1H-indazol-5-yl)but-1-en-1-yl)phenyl) acrylic acid, N-methyl glucamine salt that is characterized as having:
(a) an X-Ray powder diffraction (XRPD) pattern substantially the same as shown in FIG. 4;
(b) an X-ray powder diffraction (XRPD) pattern with characteristic peaks at 4.1±0.1° 2-Theta, 8.3±0.1° 2-Theta, 12.4±0.1° 2-Theta, 16.6±0.1° 2-Theta, 19.4±0.1° 2-Theta, 20.1±0.1° 2-Theta, 20.6±0.1° 2-Theta, 21.9±0.1° 2-Theta, 23.0±0.1° 2-Theta, 25.0±0.1° 2-Theta;
(c) an X-ray powder diffraction (XRPD) pattern post storage at 40° C. and 75% RH for at least a week that is substantially the same as that observed for the crystalline Form 1as claimed in claim 4;
(d) a DSC thermogram with an endotherm having an onset temperature at about 121° C.;
(e) a DSC thermogram substantially similar to the one set forth in FIG. 5;
(f) a TGA thermogram with 3 weight loses observed between 40-102° C., 102-143° C., and 143-346° C. degradation;
(g) A TGA thermogram substantially similar to the one set forth in FIG. 6; or
(h) combinations thereof.

14. The crystalline form of claim 13, wherein the crystalline form has an X-Ray powder diffraction (XRPD) pattern substantially the same as shown in FIG. 4.

15. The crystalline form of claim 13, wherein the crystalline form has an X-ray powder diffraction (XRPD) pattern with characteristic peaks at 4.1±0.1° 2-Theta, 12.4±0.1° 2-Theta, 16.6±0.1° 2-Theta, 19.4±0.1° 2-Theta, 21.9±0.1° 2-Theta.

16. The crystalline form of claim 13, wherein the crystalline form has a DSC thermogram with an endotherm having an onset temperature at about 121° C.

17. The crystalline form of claim 13, wherein the crystalline form has a DSC thermogram substantially similar to the one set forth in FIG. 5.

18. The crystalline form of claim 13, wherein the crystalline form has a TGA thermogram with 3 weight loses observed between 40-102° C., 102-143° C., and 143-346° C. degradation.

19. The crystalline form of claim 13, wherein the crystalline form has a TGA thermogram substantially similar to the one set forth in FIG. 6.

20. The crystalline form of claim 13, wherein the crystalline form that is characterized as having properties (a), (b), (c), (d), (e), (f), and (g).

21. The crystalline form of claim 13, wherein the crystalline form was obtained from dimethylsulfoxide.

22. The crystalline form of claim 21, wherein the crystalline form is a dimethylsulfoxide solvate.

23. A pharmaceutical composition comprising a crystalline form of claim 1, and at least one additional ingredient selected from pharmaceutically acceptable carriers, diluents and excipients.

24. The pharmaceutical composition according to claim 23, wherein the pharmaceutical composition is in a form suitable for oral administration to a mammal.

25. The pharmaceutical composition according to claim 23, wherein the pharmaceutical composition is in an oral solid dosage form.

26. The pharmaceutical composition according to claim 23, wherein the pharmaceutical composition is in the form of a tablet, capsule or pill.

27. The pharmaceutical composition according to claim 23, wherein the pharmaceutical composition comprises about 0.5 mg to about 1000 mg of crystalline (E)-3-(4-((E)-2-(2-chloro-4-fluorophenyl)-1-(1H-indazol-5-yl)but-1-en-1-yl)phenyl)acrylic acid, N-methyl glucamine salt.

28. A method of treating cancer in a mammal comprising administering crystalline (E)-3-(4-((E)-2-(2-chloro-4-fluorophenyl)-1-(1H-indazol-5-yl)but-1-en-1-yl)phenyl)acrylic acid, N-methyl glucamine salt as described in claim 4 to the mammal in need thereof, wherein the cancer is breast cancer, ovarian cancer, endometrial cancer, prostate cancer, lung cancer or uterine cancer.

* * * * *